(12) United States Patent
Chien et al.

(10) Patent No.: US 6,841,124 B2
(45) Date of Patent: Jan. 11, 2005

(54) STERILIZATION SYSTEM WITH A PLASMA GENERATOR CONTROLLED BY A DIGITAL SIGNAL PROCESSOR

(75) Inventors: John Chien, Buena Park, CA (US); Robert C. Platt, Jr., Laguna Niguel, CA (US); Anthony Lemus, Villa Park, CA (US)

(73) Assignee: Ethicon, Inc., Somerville, NJ (US)

( * ) Notice: Subject to any disclaimer, the term of this patent is extended or adjusted under 35 U.S.C. 154(b) by 91 days.

(21) Appl. No.: 10/266,063

(22) Filed: Oct. 7, 2002

(65) Prior Publication Data

US 2003/0059340 A1 Mar. 27, 2003

Related U.S. Application Data

(63) Continuation-in-part of application No. 09/812,148, filed on Mar. 19, 2001, which is a continuation-in-part of application No. 09/677,534, filed on Oct. 2, 2000, now Pat. No. 6,447,719.

(51) Int. Cl.[7] .................................................. A61L 2/00

(52) U.S. Cl. .............................. 422/3; 422/22; 422/28; 422/29; 422/62; 422/105; 422/108; 422/906

(58) Field of Search ................................ 422/3, 22, 28, 422/29, 62, 105, 108, 906

(56) References Cited

U.S. PATENT DOCUMENTS

| | | |
|---|---|---|
| 3,876,373 A | 4/1975 | Glyptis |
| 4,126,137 A | 11/1978 | Archibald |
| 4,347,541 A | 8/1982 | Chen et al. |
| 4,643,876 A | 2/1987 | Jacobs et al. |
| 4,727,874 A | 3/1988 | Bowers et al. |

(List continued on next page.)

FOREIGN PATENT DOCUMENTS

| | | |
|---|---|---|
| CA | 2302888 | 3/2000 |
| EP | 0 534 068 B1 | 6/1992 |
| EP | 0 534 068 A2 | 6/1992 |
| EP | 0 707 186 A1 | 10/1995 |
| EP | 0 831 679 A1 | 6/1996 |
| EP | 1 040 839 A1 | 3/2000 |
| EP | 1 192 953 A2 | 4/2002 |
| EP | 1 243 277 A1 | 9/2002 |
| WO | WO 01/70281 A1 | 9/2001 |

OTHER PUBLICATIONS

EPO Search Report dated Nov. 26, 2003 for EPO Appl. No. EP 03 25 63 21.
EPO Search Report dated Nov. 21, 2003 for EPO Appl. No. EP 02 251 914.
EPO Search Report dated Feb. 25, 2004 for EPO Appl. No. EP 03 25 6321.
European Search Report dated Mar. 18, 2003 re Application No. EP 01 30 8363.

Primary Examiner—Krisanne Jastrzab

(57) ABSTRACT

A sterilization system applies power to a plasma within a chamber to remove gas or vapor species from an article. The sterilization system includes a power feedback control system for controlling the power applied to the plasma. The power feedback control system includes a current monitor adapted to produce a first signal indicative of a current applied to the plasma within the chamber. The power feedback control system further includes a voltage monitor adapted to produce a second signal indicative of a voltage applied to the plasma within the chamber. The power feedback control system further includes a power control module comprising a programmable digital signal processor. The digital signal processor is adapted to receive and process the first signal and the second signal by multiplying the current and the voltage and producing a third signal indicative of the product of the current and the voltage. The power feedback control system further includes a plasma generator coupled to the power control module and adapted to adjust, in response to the third signal, the power applied to the plasma within the chamber.

25 Claims, 19 Drawing Sheets

U.S. PATENT DOCUMENTS

| | | |
|---|---|---|
| 4,751,608 A | 6/1988 | Schultz |
| 4,756,882 A | 7/1988 | Jacobs et al. |
| 4,859,926 A | 8/1989 | Wolze |
| 5,175,472 A | 12/1992 | Johnson, Jr. et al. |
| 5,203,945 A | 4/1993 | Hasegawa et al. |
| 5,302,343 A | 4/1994 | Jacob |
| 5,303,139 A | 4/1994 | Mark |
| 5,370,645 A | 12/1994 | Klicek et al. |
| 5,455,549 A | 10/1995 | Strickland et al. |
| 5,473,292 A | 12/1995 | Victorin |
| 5,474,648 A | 12/1995 | Patrick et al. |
| 5,490,197 A | 2/1996 | Albert et al. |
| 5,512,244 A | 4/1996 | Griffiths et al. |
| 5,556,549 A | 9/1996 | Patrick et al. |
| 5,565,737 A | 10/1996 | Keane |
| 5,646,569 A | 7/1997 | Bruhns et al. |
| 5,656,238 A | 8/1997 | Spencer et al. |
| 5,770,922 A | 6/1998 | Gerrish et al. |
| 5,861,752 A | 1/1999 | Klick |
| 6,060,019 A | 5/2000 | Spencer et al. |
| 6,084,205 A | 7/2000 | Sheaffer et al. |
| 6,104,487 A | 8/2000 | Buck et al. |
| 6,204,673 B1 | 3/2001 | Andeen et al. |
| 6,269,680 B1 | 8/2001 | Prieve et al. |
| 6,291,999 B1 | 9/2001 | Nishimori et al. |
| 6,365,868 B1 | 4/2002 | Borowy et al. |
| 6,383,554 B1 | 5/2002 | Chang et al. |
| 6,447,719 B1 * | 9/2002 | Agamohamadi et al. ...... 422/22 |
| 2002/0068012 A1 | 6/2002 | Agamohamadi et al. |
| 2002/0195330 A1 | 12/2002 | Agamohamadi et al. |
| 2003/0059340 A1 | 3/2003 | Chien et al. |

* cited by examiner

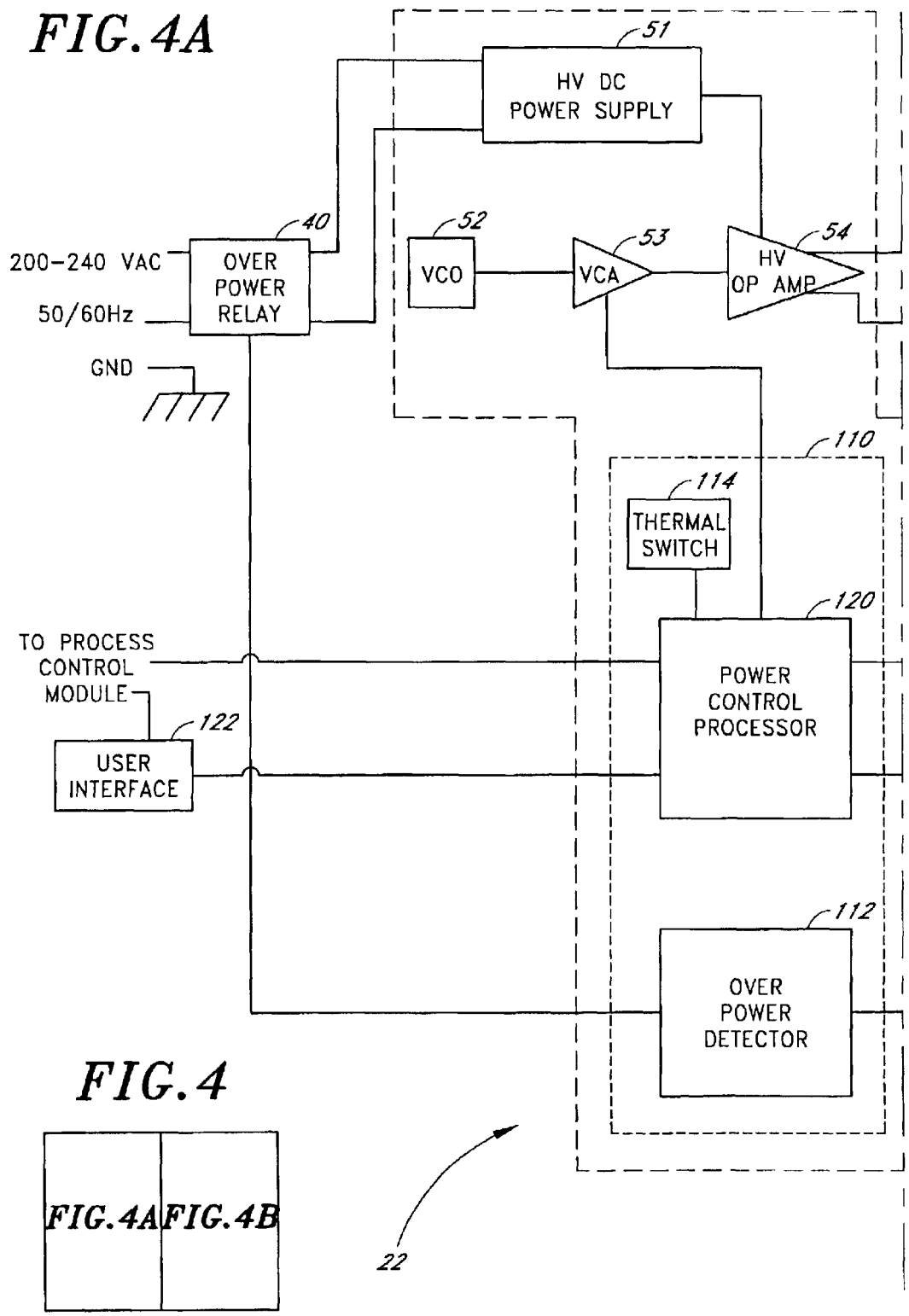
FIG. 4A
FIG. 4
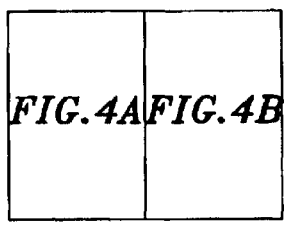

STERILIZATION SYSTEM WITH A PLASMA GENERATOR CONTROLLED BY A DIGITAL SIGNAL PROCESSOR

CLAIM OF PRIORITY

This application is a continuation-in-part of and claims priority from U.S. patent application Ser. No. 09/812,148, filed Mar. 19, 2001, which is a continuation-in-part of U.S. patent application Ser. No. 09/677,534, filed Oct. 2, 2000 and now U.S. Pat. No. 6,447,719, and both applications are incorporated in their entirety by reference herein.

BACKGROUND OF THE INVENTION

1. Field of the Invention

The invention relates to systems and methods for controlling gas discharge plasmas in sterilization systems that employ gas discharge plasmas.

2. Description of the Related Art

Plasmas produced using radio frequency (RF) generators in particular have proven to be valuable tools in processes for the sterilization of medical devices. For example, in U.S. Pat. Nos. 4,643,876 and 4,756,882, which are incorporated by reference herein, Jacobs, et al. disclose using hydrogen peroxide as a precursor in a low temperature sterilization system that employs RF plasma. The combination of hydrogen peroxide vapor and a RF plasma provides an efficient method of sterilizing medical devices without using or leaving highly toxic materials or forming toxic by-products. Similarly, Jacob, U.S. Pat. No. 5,302,343, and Griffiths, et al., U.S. Pat. No. 5,512,244, teach the use of RF plasmas in a sterilization process.

However, there are problems associated with the use of an RF plasma in a sterilization process. The RF plasma may leave residual hydrogen peroxide on the sterilized article. The residual amount of hydrogen peroxide remaining on the sterilized article depends upon the RF power applied to the article, the amount of time exposed to the RF plasma, and the material of the article. For example, while some plastics (e.g., polyurethane) absorb hydrogen peroxide, other materials (e.g., Teflon) absorb relatively little, thereby yielding less residual hydrogen peroxide after sterilization.

In addition, inherent inefficiencies in the energy conversion from the low frequency (e.g., 60 Hz) line voltage to the RF (e.g., approximately 1 MHz–1 GHz) voltage used to generate the RF plasma limit the power efficiency of such systems to typically less than 50%. Energy efficiency is further reduced by typically 5–20% by virtue of the losses from the required impedance matching network between the RF generator and the load. Such low energy efficiency significantly increases the cost per watt applied to the sterilized articles. The required instrumentation for using RF electrical energy (e.g., RF generator, impedance matching network, monitoring circuitry) is expensive, which also increases the cost per watt applied to the sterilized articles.

SUMMARY OF THE INVENTION

A sterilization system applies power to a plasma within a chamber to remove gas or vapor species from an article. The sterilization system comprises a power feedback control system for controlling the power applied to the plasma. The power feedback control system comprises a current monitor adapted to produce a first signal indicative of a current applied to the plasma within the chamber. The power feedback control system further comprises a voltage monitor adapted to produce a second signal indicative of a voltage applied to the plasma within the chamber. The power feedback control system further comprises a power control module comprising a programmable digital signal processor. The digital signal processor is adapted to receive and process the first signal and the second signal by multiplying the current and the voltage and producing a third signal indicative of the product of the current and the voltage. The power feedback control system further comprises a plasma generator coupled to the power control module and adapted to adjust, in response to the third signal, the power applied to the plasma within the chamber.

A method applies power to a plasma within a chamber to remove gas or vapor species from an article. The method comprises producing a first signal indicative of a current applied to the plasma within the chamber. The method further comprises producing a second signal indicative of a voltage applied to the plasma within the chamber. The method further comprises producing a third signal in response to the first signal and the second signal. The third signal is produced using a programmable digital signal processor that multiplies the current and the voltage. The third signal is indicative of the product of the current and the voltage. The method further comprises adjusting the power applied to the plasma in response to the third signal.

A sterilization system applies power to a plasma within a chamber to remove gas or vapor species from an article. The sterilization system comprises a power feedback control system for controlling the power applied to the plasma. The power has a waveform frequency. The power feedback control system comprises a current monitor adapted to produce a first signal indicative of a current applied to the plasma within the chamber. The power feedback control system further comprises a voltage monitor adapted to produce a second signal indicative of a voltage applied to the plasma within the chamber. The power feedback control system further comprises a power control module adapted to produce a third signal in response to the first signal and the second signal. The power control module has a processing speed faster than the inverse of the waveform frequency. The power feedback control system further comprises a plasma generator coupled to the power control module. The plasma generator is adapted to adjust, in response to the third signal, the power applied to the plasma within the chamber.

A sterilization system applies a power wavetrain to a plasma within a chamber to remove gas or vapor species from an article. The power wavetrain comprises a plurality of power pulses having a characteristic pulse period. The sterilization system comprises a power feedback control system for controlling the power applied to the plasma. The power feedback control system comprises a current monitor adapted to produce a first signal indicative of a current applied to the plasma within the chamber. The power feedback control system further comprises a voltage monitor adapted to produce a second signal indicative of a voltage applied to the plasma within the chamber. The first and second signal are produced on a time scale shorter than the characteristic pulse period. The power feedback control system further comprises a power control module adapted to monitor the first signal and the second signal and to produce a third signal in response to the first signal and the second signal. The third signal is produced on a time scale shorter than the characteristic pulse period. The power feedback control system further comprises a plasma generator coupled to the power control module. The plasma generator is adapted to adjust, in response to the third signal, the power applied to the plasma within the chamber. The power applied to the plasma is adjusted on a time scale shorter than the characteristic pulse period, thereby providing intra-pulse monitoring and control of the power applied to the plasma.

DETAILED DESCRIPTION

Production of gas discharge plasmas using low frequency (LF) voltages avoids the various problems inherent in the state of the art sterilization devices and processes which form and use plasmas produced by radio frequency (RF) voltages. First, LF plasma processing leaves less residual reactive species remaining on the sterilized articles than does RF plasma processing. Second, generation of the LF plasma is highly energy efficient because little or no frequency conversion from the line voltage is needed. For example, by using no frequency conversion with a line voltage frequency of 60 Hz, the energy efficiency of the sterilization system can reach approximately 85–99%. Use of LF voltages also does not require an impedance matching network, thereby avoiding the associated energy losses. Third, due to the simplified instrumentation and higher energy efficiency of LF generation, the cost per watt applied to the sterilized articles using LF plasmas can be as low as one-tenth the cost per watt of using RF plasmas. Fourth, the simplified instrumentation used for generating LF plasmas has proven to be more reliable and robust, and requiring less complicated diagnostic instrumentation.

Figure 1:
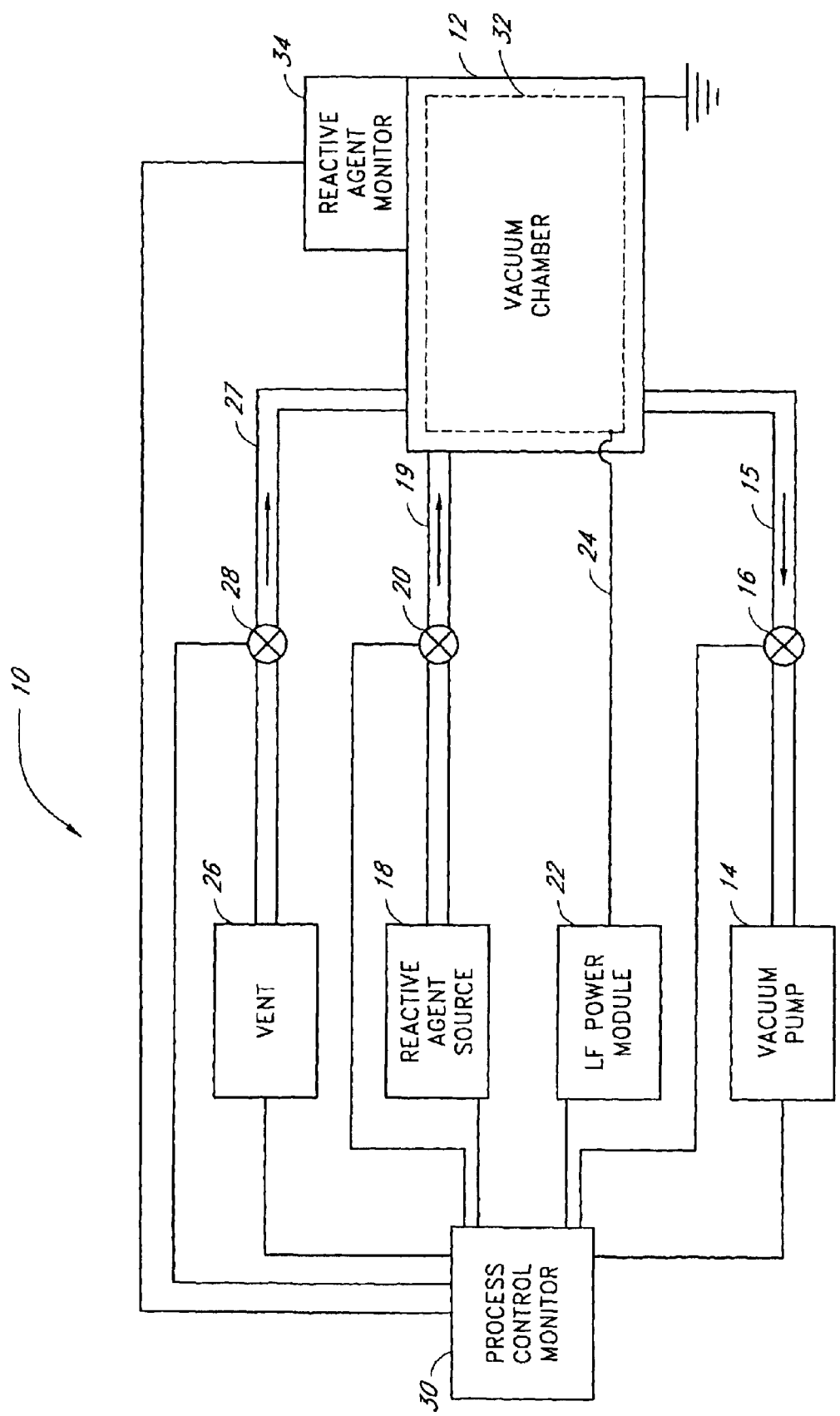
FIG. 1 schematically illustrates an embodiment of a sterilization system.

FIG. 1 schematically illustrates one embodiment comprising a sterilization system 10. The sterilization system 10 comprises a vacuum chamber 12, a vacuum pump 14, a vacuum pump line 15, a vacuum pump valve 16, a reactive agent source 18, a reactive agent line 19, a reactive agent valve 20, a low frequency (LF) power module 22, an LF voltage conduit 24, a vent 26, a vent line 27, a vent valve 28, a process control module 30, an electrode 32, and a reactive agent monitor 34. Persons skilled in the art recognize that other sterilization systems of different configurations than that illustrated in FIG. 1 are compatible with embodiments described herein.

In certain embodiments, the articles (not shown in FIG. 1) to be sterilized are packaged in various commonly employed packaging materials used for sterilized products. The preferred materials are spunbonded polyethylene packaging material commonly available under the trademark "TYVEK" or composites of "TYVEK" with a polyethylene terephthalate packaging material commonly available under the trademark "MYLAR". Other similar packaging materials may also be employed such as polypropylene. Paper packaging materials may also be used. With paper packaging, longer processing times may be required to achieve sterilization because of possible interactions of the reactive agent with paper.

The vacuum chamber 12 of certain embodiments is sufficiently gas-tight to support a vacuum of approximately less than 40 Pa (0.3 Torr). Coupled to the vacuum chamber 12 is a pressure monitor (not shown) which is also coupled to the process control module to provide a measure of the total pressure within the vacuum chamber. Also coupled to the vacuum chamber 12 is the reactive agent monitor 34 which is capable of detecting the amount of the reactive agent in the vacuum chamber 12. In an exemplary embodiment, the reactive agent is hydrogen peroxide, and the reactive agent monitor 34 measures the absorption of ultraviolet radiation at a wavelength characteristic of hydrogen peroxide. Other methods of reactive agent detection compatible with embodiments described herein include, but are not limited to, pressure measurement, near infrared absorption, and dew point measurement. The reactive agent monitor 34 is also coupled to the process control module 30 to communicate the detected amount of the reactive agent to the process control module 30.

In certain embodiments, inside and electrically isolated from the vacuum chamber 12 is the electrode 32, which is electrically conductive and perforated to enhance fluid communication between the gas and plasma species on each side of the electrode 32. The electrode 32 of certain embodiments generally conforms to the inner surface of the vacuum chamber 12, spaced approximately one-half to two inches from the wall of the vacuum chamber 12, thereby defining a gap region between the vacuum chamber 12 and the electrode 32. The electrode 32 is coupled to the LF power module 22 via the LF voltage conduit 24. In certain embodiments, with the vacuum chamber 12 connected to electrical ground, application of an LF voltage between the vacuum chamber 12 and the electrode 32 creates an LF electric field which is stronger in a first region 31 which includes the gap region and the vicinity of the edges of the electrode 32. The LF electric field is weaker in a second region 33 where the sterilized articles are placed. Generally, in other embodiments, the LF electric field can be generated by applying an LF voltage between the electrode 32 and a second electrode in the vacuum chamber 12. In such embodiments, the first region 31 includes the gap region between the two electrodes, and the vicinity of the edges of one or both of the electrodes. An embodiment in which the vacuum chamber 12 serves as the second electrode is one of the many different ways to generate the gas plasma.

Figure 2A:
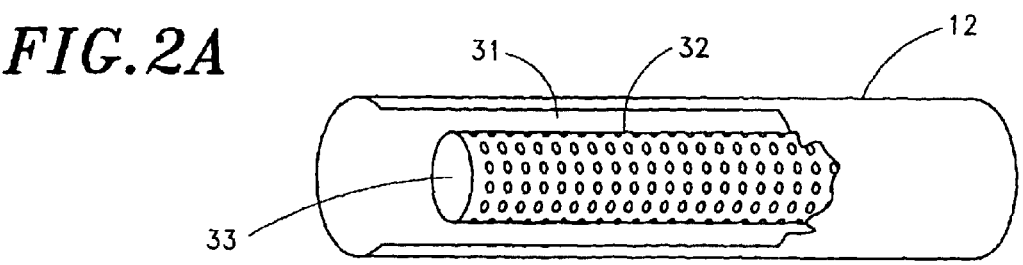
FIG. 2A schematically illustrates an embodiment of a cylindrically-shaped electrode with open ends and perforated sides.
Figure 2B:
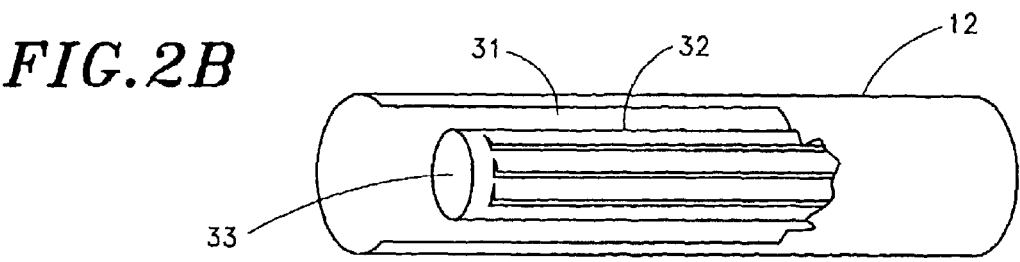
FIG. 2B schematically illustrates an embodiment of a cylindrically-shaped electrode with open ends and louvered sides.
Figure 2C:
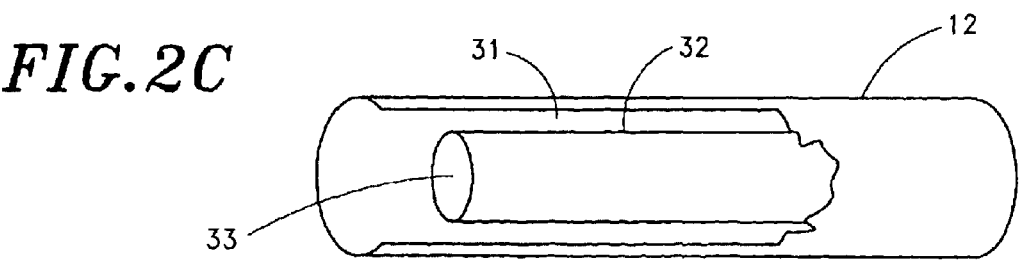
FIG. 2C schematically illustrates an embodiment of a cylindrically-shaped electrode with open ends and solid sides.
Figure 2D:
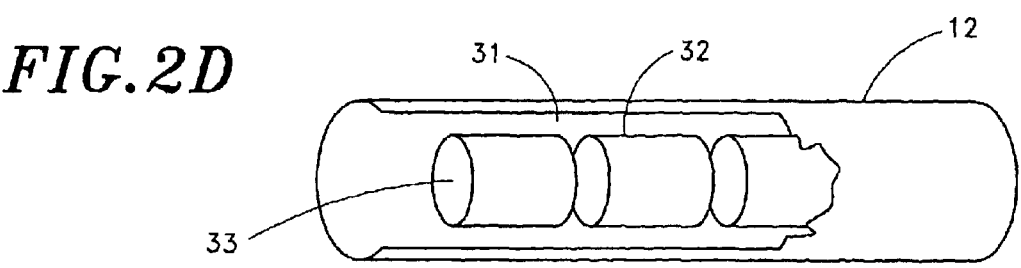
FIG. 2D schematically illustrates an embodiment of an electrode comprising one or more collinear cylindrically-shaped segments with open ends and solid sides.
Figure 2E:
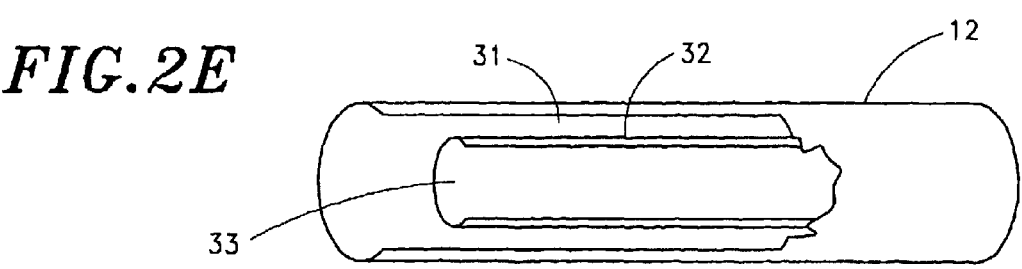
FIG. 2E schematically illustrates an embodiment of an electrode with a partial cylindrical shape, open ends, and solid sides.
Figure 2F:
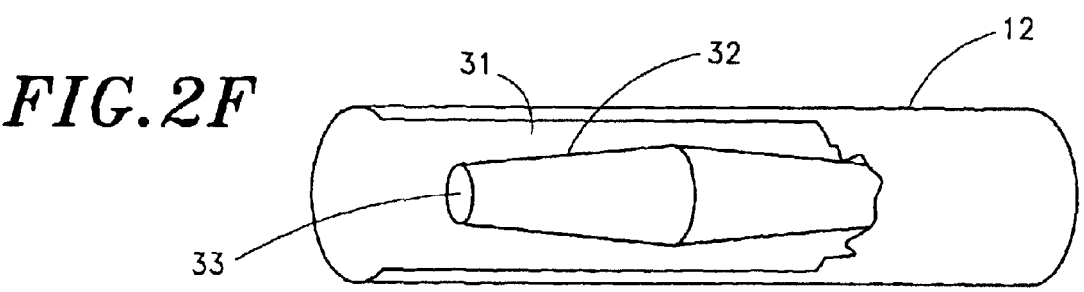
FIG. 2F schematically illustrates an embodiment of a cylindrically-symmetric and longitudinally-asymmetric electrode with open ends and solid sides.
Figure 2G:
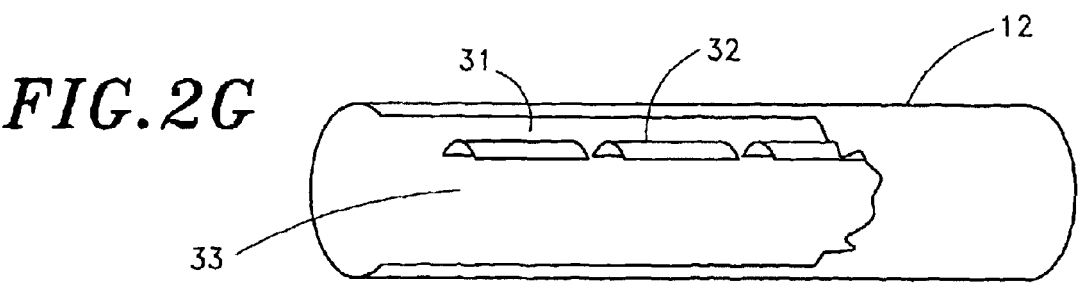
FIG. 2G schematically illustrates an embodiment of one or more asymmetric electrodes with open ends and solid sides.
Figure 2H:
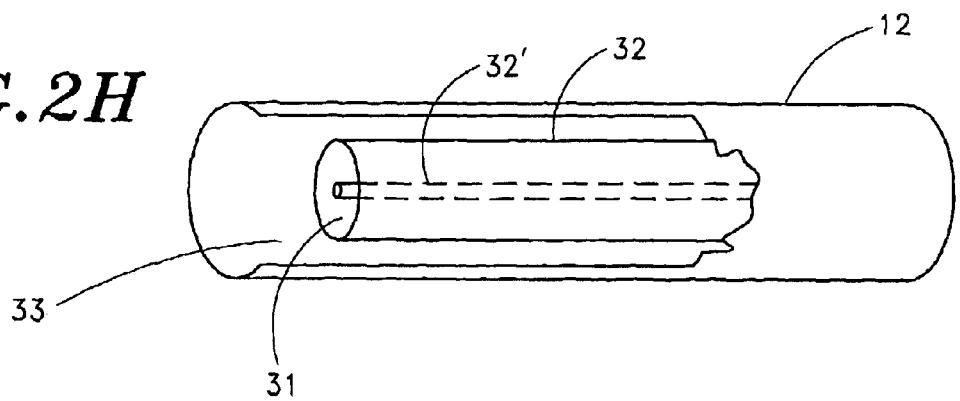
FIG. 2H schematically illustrates an embodiment of an electrode system with a first electrode that is cylindrically-shaped with open ends and solid sides, and a second electrode comprising a wire substantially collinear with the first electrode.
Figure 2I:
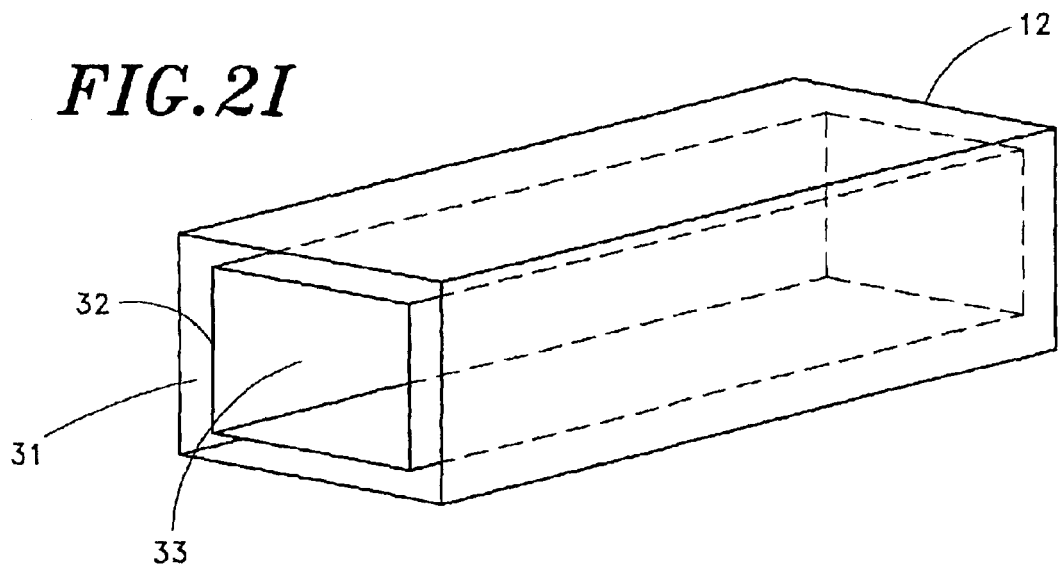
FIG. 2I schematically illustrates an embodiment of a generally square or rectangular electrode within a generally square or rectangular vacuum chamber.

In the embodiment illustrated in FIG. 2A, a cylindrically-shaped electrode 32 provides fluid communication between the gas and plasma on each side of the electrode 32 through the open ends of the electrode 32 as well as through the perforations in the side of the electrode 32. These open ends and perforations permit gaseous and plasma species to freely travel between the first region 31 between the electrode 32 and the walls of the vacuum chamber 12 and the second region 33 where the sterilized articles are placed. Similarly, as illustrated in FIGS. 2B–2I, other configurations of the electrode 32 provide fluid communication between the first region 31 and the second region 33. FIG. 2B schematically illustrates a cylindrically-shaped electrode 32 with open ends and louvered openings along its sides. FIG. 2C schematically illustrates a cylindrically-shaped electrode 32 with open ends and solid sides. FIG. 2D schematically illustrates an electrode 32 comprising a series of collinear cylindrically-shaped segments with open ends and solid sides. FIG. 2E schematically illustrates an electrode 32 with a partial cylindrical shape, open ends and solid sides. FIG. 2F schematically illustrates a cylindrically-symmetric and longitudinally-asymmetric electrode 32 with open ends and solid sides. FIG. 2G schematically illustrates an asymmetric electrode 32 with open ends and solid sides. More than one electrode can be used to generate the plasma. FIG. 2H schematically illustrates an electrode system with a first electrode 32 that is cylindrically-shaped with open ends and solid sides, and a second electrode 32' comprising a wire substantially collinear with the first electrode 32. The LF voltage is applied between the first electrode 32 and the second electrode 32'. In this embodiment, the first region 31 is the region between the first electrode 32 and the second electrode 32', and the second region 33 is between the first electrode 32 and the vacuum chamber 12. FIG. 2I schematically illustrates a generally square or rectangular electrode within a generally square or rectangular vacuum chamber. The various configurations for generally cylindrical electrodes schematically illustrated in FIGS. 2A–2H can also be applied to the generally square or rectangular electrode of FIG. 2I. Each of these embodiments of the electrode 32 provide fluid communication between the first region 31 and the second region 33.

The vacuum pump 14 of certain embodiments is coupled to the vacuum chamber 12 via the vacuum pump line 15 and the vacuum valve 16. Both the vacuum pump 14 and the vacuum pump valve 16 are coupled to, and controlled by, the process control module 30. By opening the vacuum valve 16, gases within the vacuum chamber 12 are pumped out of the vacuum chamber 12 through the vacuum pump line 15 by the vacuum pump 14. In certain embodiments, the vacuum valve 16 is capable of being opened to variable degrees to adjust and control the pressure in the vacuum chamber 12.

The reactive agent source 18 of certain embodiments is a source of fluid coupled to the vacuum chamber 12 via the reactive agent line 19 and the reactive agent valve 20. The reactive agent valve 20 is coupled to, and controlled by, the process control module 30. The reactive agent source 18 of certain embodiments comprises reactive agent species. In such embodiments, the reactive agent species comprises a germicide which is a sterilant or a disinfectant, such as hydrogen peroxide. In addition, the germicide supplied by the reactive agent source 18 can be in gas or vapor form. By opening the reactive agent valve 20, reactive agent atoms and molecules from the reactive agent source 18 can be transported into the vacuum chamber 12 via the reactive agent line 19. In certain embodiments, the reactive agent valve 20 is capable of being opened to variable degrees to adjust the pressure of the reactive agent in the vacuum chamber 12. In an exemplary embodiment, the reactive agent species of the reactive agent source 18 comprising hydrogen peroxide molecules.

The vent 26 of certain embodiments is coupled to the vacuum chamber 12 via the vent line 27 and the vent valve 28. The vent valve 28 is coupled to, and controlled by, the process control module 30. By opening the vent valve 28, vent gas is vented into the vacuum chamber 12 via the vent line 27. In certain embodiments, the vent valve 28 is capable of being opened to variable degrees to adjust the pressure of the air in the vacuum chamber 12. In an exemplary embodiment, the vent 26 is a High Efficiency Particulate-filtered Air (HEPA) vent which provides filtered air as the vent gas. Other vent gases compatible with embodiments described herein include, but are not limited to, dry nitrogen, and argon.

The process control module 30 is coupled to various components of the sterilization system 10 to control the sterilization system 10. In an exemplary embodiment, the process control module 30 is a microprocessor configured to provide control signals to the various other components in response to the various signals received from other components.

Figures 3, 3A:
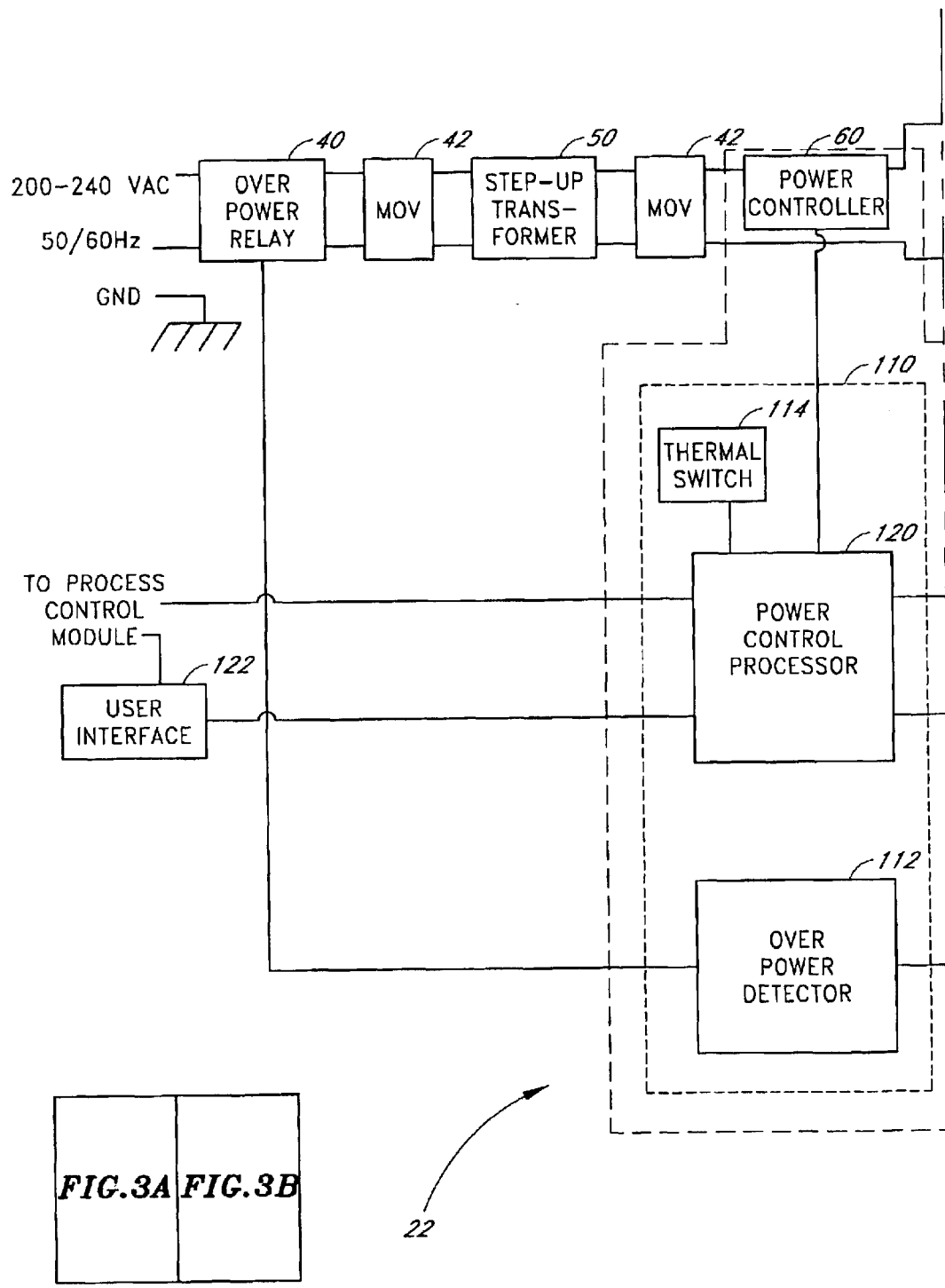
FIG. 3, which is broken into FIGS. 3A and 3B, schematically illustrates an embodiment of a low frequency power module compatible with the phase angle control method.
Figure 3B:
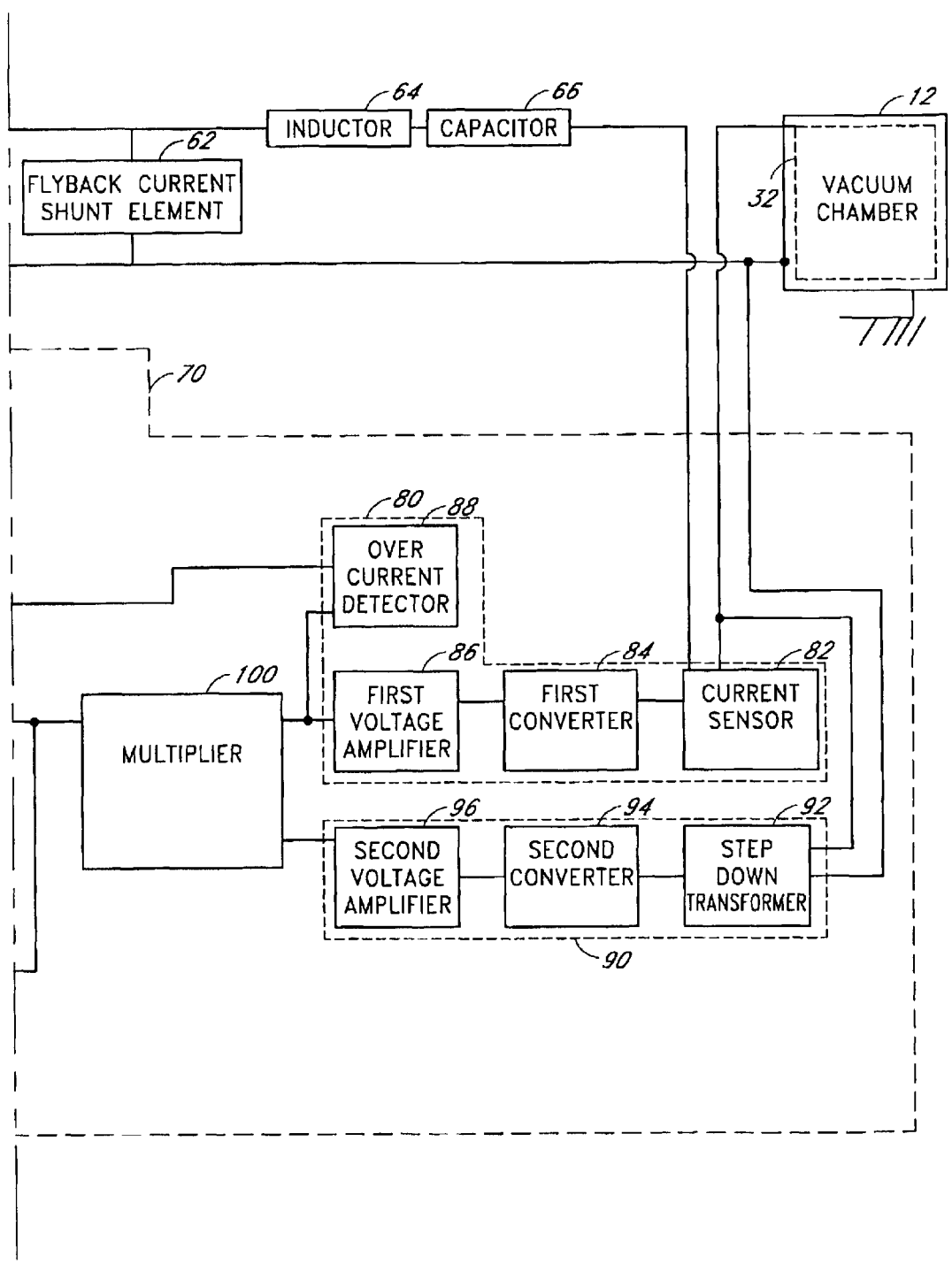

The LF power module 22 of certain embodiments is coupled to the electrode 32 via the LF voltage conduit 24, and is coupled to, and controlled by, the process control module 30. The LF power module 22 is adapted to apply a low frequency voltage between the electrode 32 and the vacuum chamber 12 so as to generate a plasma in the vacuum chamber 12. FIG. 3, which is broken into FIGS. 3a and 3b, schematically illustrates an embodiment of the LF power module 22 compatible with the phase angle control method of controlling the low frequency power applied to the plasma. As illustrated in FIG. 3, the LF power module 22 comprises an over-power relay 40, a pair of metal oxide varistors 42, a step-up transformer 50, a flyback current shunt element 62, an inductor 64, a capacitor 66, and a LF power feedback control system 70. The LF power feedback control system 70 illustrated in FIG. 3 comprises a power controller 60, a current monitor 80, a voltage monitor 90, and a power monitor 100 coupled to the current monitor 80 and the voltage monitor 90. Line voltage (typically 200–240 VAC, 50/60 Hz) is provided to the step-up transformer 50 via the closed over-power relay 40 which is coupled to the LF power feedback control system 70.

In the embodiment illustrated in FIG. 3, the metal oxide varistors (MOVs) 42 are used to suppress transient voltage impulses. Each MOV 42 is a multiple-junction solid-state device capable of withstanding large magnitude impulses with a low amount of let-through voltage. The MOVs 42 serve as fast acting "variable resistors" with a low impedance at higher-than-normal voltages and a high impedance at normal voltages. MOVs are manufactured for specific voltage configurations and for a variety of impulse magnitudes. Persons skilled in the art are able to select MOVs 42 consistent with embodiments described herein.

The output voltage of the step-up transformer 50 is preferably between approximately 100 and 1000 $V_{rms}$, more preferably between approximately 200 and 500 $V_{rms}$, and most preferably between approximately 250 and 450 $V_{rms}$. The output voltage of the step-up transformer 50 is transmitted to the power controller 60, which provides the LF voltage to the electrode 32 and vacuum chamber 12 via the flyback current shunt element 62, the inductor 64, the capacitor 66, and the LF power feedback control system 70. The flyback current shunt element 62 provides a path for fly-back current and to tune the circuit, and in certain embodiments the flyback current shunt element 62 is a load resistor of approximately 1500 ohms. In other embodiments, the flyback current shunt element 62 can be a snubber. The inductance of the inductor 64 is chosen to limit noise spikes in the LF current, and is typically approximately 500 mH. The capacitance of the capacitor 66 is chosen to maximize the efficiency of power transfer to the LF plasma by matching the resonant frequency of the series LC circuit to the frequency of the applied LF voltage. For a 60 Hz voltage and an inductance of 500 mH, a capacitance of approximately 13.6 $\mu F$ provides the resonant condition for which the impedance of the series LC circuit is approximately zero, thereby maximizing the transmitted LF power. Persons skilled in the art are able to select appropriate values for these components depending on the frequency of the applied LF voltage in a manner compatible with embodiments described herein.

Figure 4B:
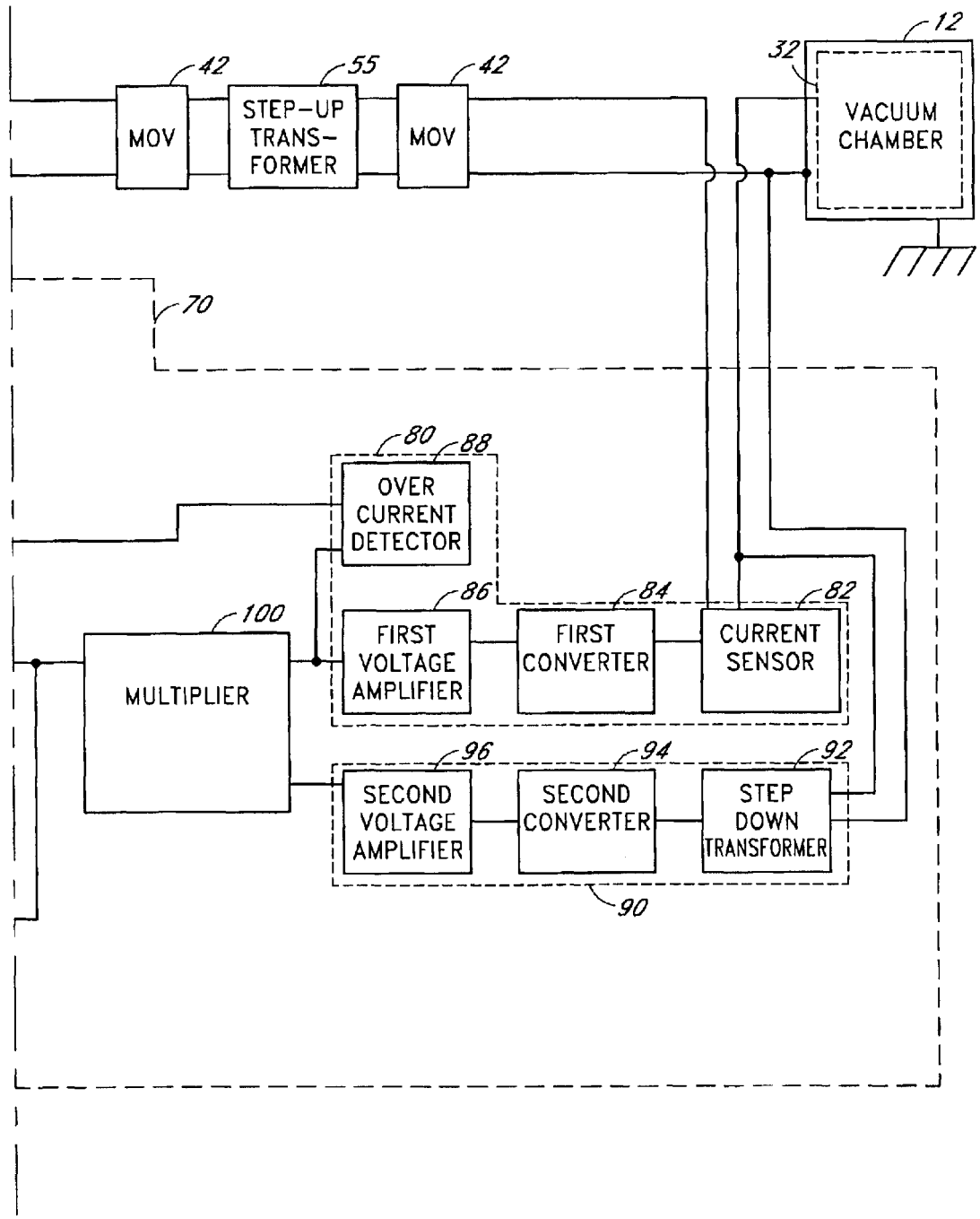
FIG. 4, which is broken into FIGS. 4A and 4B, schematically illustrates an embodiment of a low frequency power module compatible with the amplitude control method.

FIG. 4, which is broken into FIGS. 4a and 4b, schematically illustrates an embodiment of the LF power module 22 compatible with the amplitude control method of controlling the low frequency power applied to the plasma. As illustrated in FIG. 4, the LF power module 22 comprises an over-power relay 40, a pair of metal oxide varistors 42, a step-up transformer 55, and a LF power feedback control system 70. The LF power feedback control system 70 illustrated in FIG. 4 comprises a high voltage (HV) DC power supply 51, a voltage-controlled oscillator (VCO) 52, a voltage-controlled amplifier (VCA) 53, a HV operational amplifier 54, a current monitor 80, a voltage monitor 90, and a power monitor 100 coupled to the current monitor 80 and the voltage monitor 90. Line voltage is provided to the HV DC power supply 51 via the closed over-power relay 40 which is coupled to the LF power feedback control system 70. The output of the HV DC power supply 51 is preferably between approximately 100 and 1000 VDC, more preferably between approximately 200 and 500 VDC, and most preferably between approximately 250 and 450 VDC.

In the embodiment illustrated in FIG. 4, the VCO 52 generates a sinewave output with a constant amplitude and fixed low frequency less than or equal to approximately 200 kHz (which includes DC voltages and currents), the low frequency selected by supplying an appropriate set-point voltage to the VCO 52. Alternative embodiments can utilize other waveforms, e.g., triangular or square waveforms. The LF output of the VCO 52 is supplied to the VCA 53, which serves as a power controller to maintain a substantially stable average LF power applied to the plasma. In response to a feedback signal from the power control module 110, the VCA 53 amplifies the LF output of the VCO 52 to generate an amplified LF voltage with an amplitude between approximately 0 and 12 VAC. The amplified LF voltage from the VCA 53 is supplied to the HV operational amplifier 54 which in response generates a high voltage LF output with an amplitude determined by the amplitude of the amplified LF voltage from the VCA 53. Appropriate HV operational amplifiers are commercially available (e.g., Apex Microtechnology, Tucson, Ariz., part number PA93), and persons skilled in the art are able to select a HV operational amplifier compatible with embodiments described herein. Typically, the amplitude of the high voltage LF output from the HV operational amplifier 54 is approximately 100 to 150 VAC. In order to generate larger amplitude LF voltages to be applied to the plasma, the high voltage LF output from the HV operational amplifier 54 can be further amplified by the step-up transformer 55, as illustrated in FIG. 4. Alternatively, the step-up transformer 55 may be omitted if the HV operational amplifier 54 is capable of generating a high voltage LF output with the desired amplitude to be applied to the plasma.

In both the phase angle control embodiment illustrated in FIG. 3 and the amplitude control embodiment illustrated in FIG. 4, the LF power feedback control system 70 of the LF power module 22 further comprises a power control module 110 coupled to the power monitor 100, which is coupled to the current monitor 80 and voltage monitor 90. The current monitor 80 measures the LF current through the electrode 32 and the vacuum chamber 12. In certain embodiments, the current monitor 80 includes a current sensor 82 which provides a voltage output indicative of the measured real-time, cycle-by-cycle LF current, a first converter 84 which produces a DC voltage in response to the RMS of the voltage output of the current sensor 82, and a first voltage amplifier 86 which amplifies the DC voltage from the first converter 84 to produce a real-time current signal. In addition, the current monitor 80 also includes an over-current detector 88, which monitors the DC voltage from the first converter 84 in real-time and sends an error signal to the power control module 110 if the LF current exceeds a pre-set value, caused for example by a plasma instability between the electrode 32 and the vacuum chamber 12. Under such an occurrence, the LF voltage is turned off momentarily. This occurrence can result in a few cycles being lost, however the LF power is stabilized so that the average power is not affected by more than a predetermined tolerance.

The voltage monitor 90 measures the LF voltage between the electrode 32 and the vacuum chamber 12. In certain embodiments, the voltage monitor 90 includes a step-down transformer 92 which produces a voltage output indicative of the measured real-time, cycle-by-cycle LF voltage, a second converter 94 which produces a DC voltage in response to the RMS of the voltage output of the step-down transformer 92, and a second voltage amplifier 96 which amplifies the DC voltage from the second converter 94 to produce a real-time voltage signal. In other embodiments, the voltage output from the step-down transformer 92 and the voltage output of the current sensor 82 are multiplied together and directed to a single converter which creates a voltage signal corresponding to the power applied to the plasma.

In certain embodiments, the power monitor 100 further comprises a multiplier that receives the DC voltages from the current monitor 80 and the voltage monitor 90, and multiplies these two voltages to produce a real-time power signal proportional to the LF power applied to the plasma between the electrode 32 and the vacuum chamber 12, the real-time power signal being generated in response to the real-time current and real-time voltage signals, and transmitted to the power control module 110. In other embodiments, the power monitor 100 monitors the LF power applied to the plasma by utilizing a signal indicative of the real-time impedance of the plasma with either the real-time current or real-time voltage signals. In still other embodiments, the power monitor 100 monitors the LF power applied to the plasma by utilizing other real-time signals which indirectly indicate the LF power applied to the plasma; e.g., a real-time signal proportional to the brightness of the glow discharge generated by the plasma. Persons skilled in the art can select an appropriate power monitor 100 compatible with embodiments described herein.

The power control module 110 of certain embodiments includes a fault detector, such as an over-power detector 112 which monitors the real-time power signal from the power monitor 100 and opens the over-power relay 40 if the LF power exceeds a pre-set value, thereby extinguishing the LF plasma. After such an occurrence, the control of restart can be given to the user or to software. The power control module 110 of certain embodiments further comprises an additional fault detector, such as a thermal switch 114 which detects overheating, and a power control processor 120.

In certain embodiments, the power control processor 120 controls and monitors the status of the LF power feedback control system 70. The power control processor 120 is coupled to a user interface 122 which provides user input regarding a selected power magnitude setting and a selected power on/off setting. The power control processor 120 is also coupled to the power monitor 100, the thermal switch 114, and the over-current detector 88. In certain embodiments, the power magnitude setting can be selected from two power levels. When the LF power is turned on, certain embodiments of the power control processor 120 ensure that a "soft start" condition is maintained in which the inrush current is minimized. In addition, the user interface 122 receives signals from the power control processor 120 indicative of the status of the sterilization system 10, which is communicated to the user.

In the phase angle control embodiment illustrated in FIG. 3, the power control processor 120 is also coupled to the power controller 60. In this embodiment, the power control processor 120 transmits a signal to the power controller 60 in response to signals from the user interface 122, power monitor 100, over-current detector 88, and thermal switch 114 in order to maintain a substantially stable LF power applied to the LF plasma while avoiding error conditions. In the amplitude control embodiment illustrated in FIG. 4, the power control processor 120 is coupled to the VCA 53. In this embodiment, the power control processor 120 transmits a signal to the VCA 53 in response to signals from the user interface 122, power monitor 100, over-current detector 88, and thermal switch 114 in order to maintain a substantially stable LF power applied to the LF plasma while avoiding error conditions. In both embodiments illustrated in FIG. 3 and FIG. 4, the power control processor 120 typically maintains the LF power applied to the LF plasma within a tolerance of approximately 0–5% of the specified power level.

Note that not all of the components listed and described in FIG. 3 and FIG. 4 are required to practice embodiments described herein, since FIG. 3 and FIG. 4 merely illustrate particular embodiments of the LF power module 22. These components include components for automation, safety, regulatory, efficiency, and convenience purposes. Other embodiments can eliminate some or all of these components, or can include additional components.

Figure 5A:
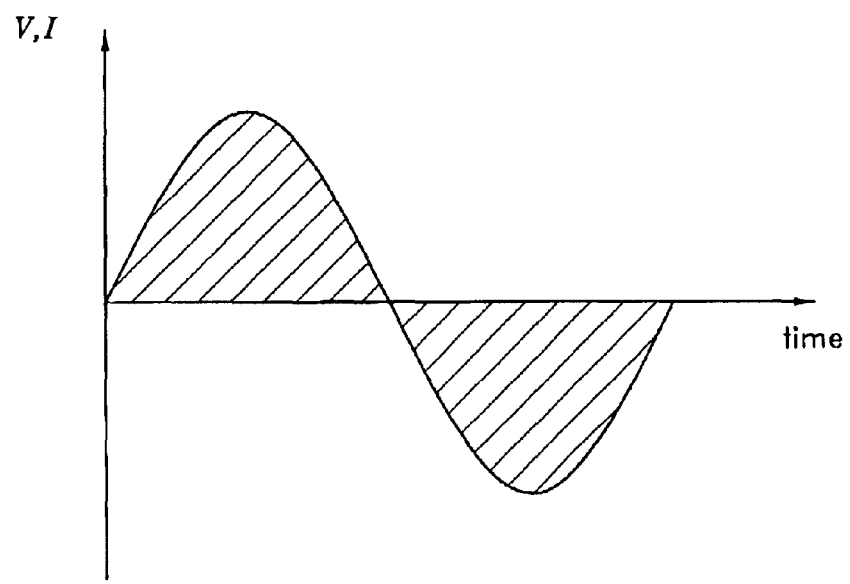
FIG. 5A schematically illustrates the phase angle control method of controlling the low frequency power applied to the plasma.
Figure 5A:
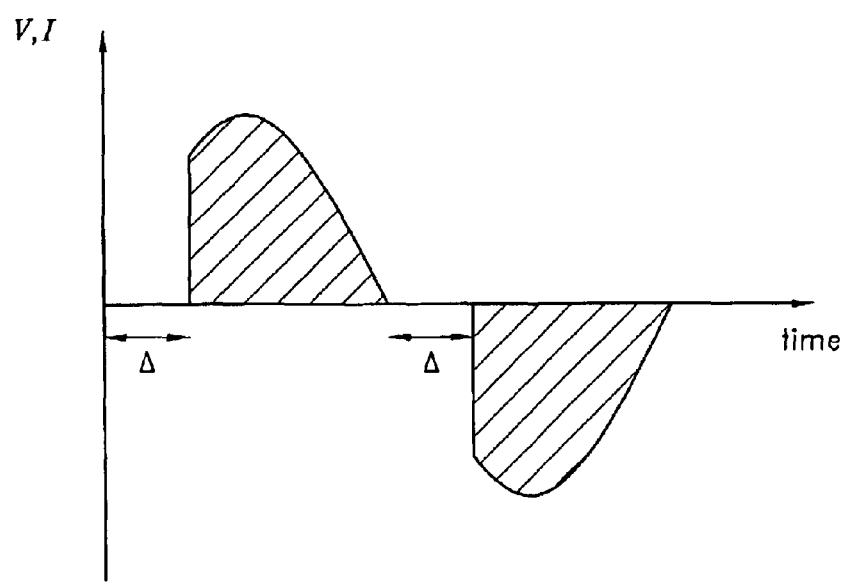

In response to the signal from the power control processor 120, the power controller 60 of the embodiment illustrated in FIG. 3 controls the LF power applied between the electrode 32 and the vacuum chamber 12 by utilizing phase angle control. Under phase angle control, the duty cycle of the LF power is modified by zeroing the voltage and current applied between the electrode 32 and the vacuum chamber 12 for a portion $\Delta$ of the cycle period. Such phase angle control is often used to maintain constant power from electric heaters or furnaces. FIG. 5A schematically illustrates the voltage and current for a 100% duty cycle (i.e., $\Delta=0$) and for a reduced duty cycle (i.e., $\Delta \neq 0$). During normal operations, the power controller 60 maintains a constant LF power applied to the plasma by actively adjusting the duty cycle of the LF power in response to the feedback real-time signal received from the power control module 110 in response to the measured LF power. When a fault event is detected by the over-current detector 88 or thermal switch 114, the power control processor 120 reduces the LF power by reducing the duty cycle of the LF power, and it transmits a signal to the user interface 122 to provide notification of the fault event. Persons skilled in the art are able to select appropriate circuitry to modify the duty cycle of the LF power consistent with embodiments described herein.

Figure 5B:
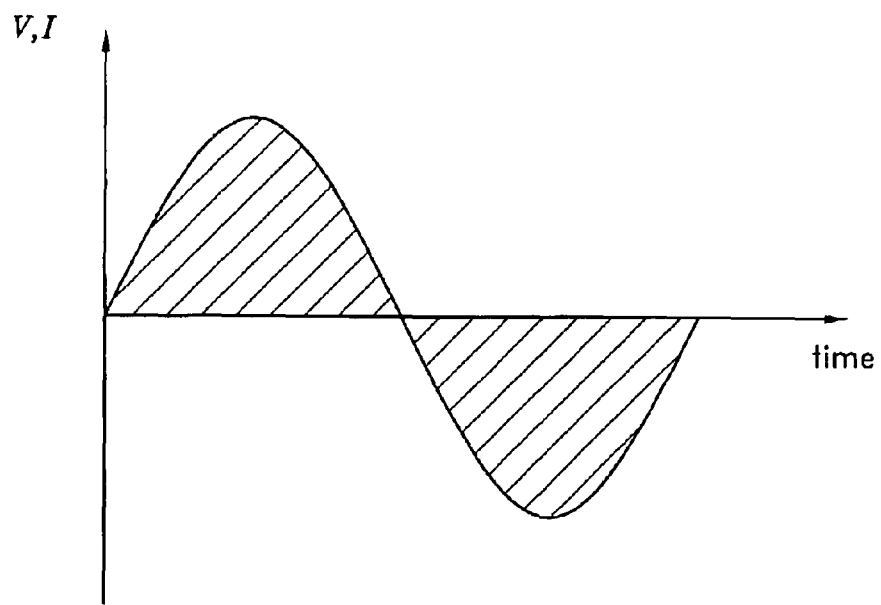
FIG. 5B schematically illustrates the amplitude control method of controlling the low frequency power applied to the plasma.
Figure 5B:
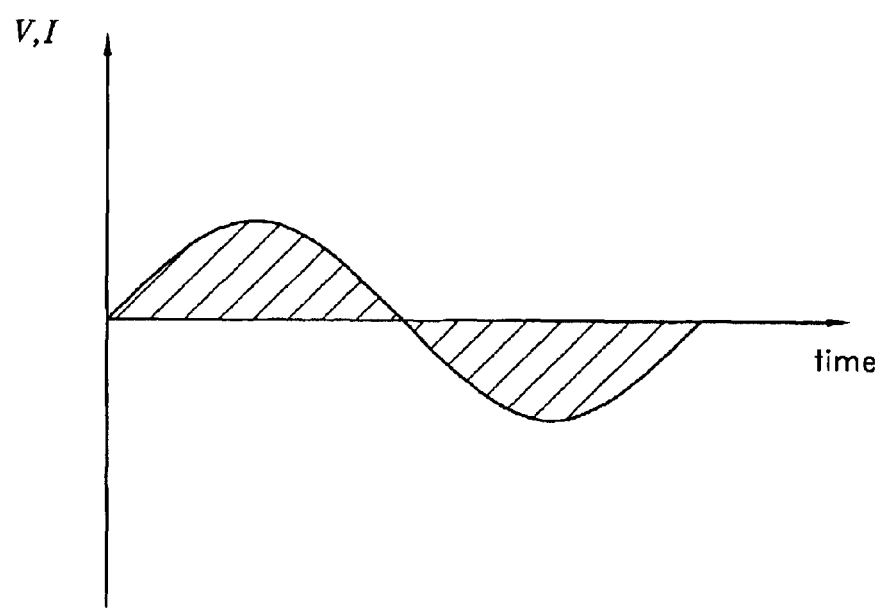

Alternatively, the LF power can be controlled by utilizing amplitude control, as in the embodiment illustrated in FIG. 4. Under amplitude control, the LF power is modified by adjusting the amplitude of the voltage and current applied between the electrode 32 and the vacuum chamber 12. FIG. 5B schematically illustrates the voltage and current corresponding to a first LF power setting and a second LF power setting less than the first LF power setting. During normal operations, the VCA 53 maintains a constant LF power applied to the plasma by actively adjusting the amplitude of the LF power in response to the feedback real-time signal received from the power control module 110 in response to the measured LF power. Persons skilled in the art are able to select appropriate circuitry to modify the amplitude of the LF power consistent with embodiments described herein.

The electronics for RF sterilizers are complicated by the need of such systems to attempt to closely match the output impedance of the RF generator with the plasma impedance at all times in order to maximize power efficiency and to avoid damage to the RF generator. Plasma impedance varies widely during plasma formation, being very high until the plasma is fully formed, and very low thereafter. When first igniting a plasma, the RF generator cannot match the high plasma impedance which exists prior to the full formation of the plasma, so a large fraction of the power output is reflected back to the RF generator. RF generators have protection systems which typically limit the RF generator output during periods of high reflected power to avoid damage. However, to ignite the plasma, the voltage output of the RF generator must exceed the threshold voltage required for plasma ignition. The threshold voltage is dependent on the chamber pressure, reactive agent, and other operating geometries and parameters and is approximately 300 $V_{rms}$ in certain embodiments. In an RF system, once ignition has been achieved, and the plasma impedance is thereby reduced, the magnitude of the applied RF voltage must be reduced to a sustaining voltage, e.g., approximately 140 $V_{rms}$ to avoid excessive power delivery. Because the higher RF voltages required for plasma ignition produce excessively high reflected power before full plasma formation, RF generators require complicated safeguards to prevent damage during the plasma ignition stage.

Conversely, the complexity of the power system and rate of ignition failures are significantly reduced for LF sterilizers since the LF sterilizers may operate using applied voltages above the threshold voltage and have much less restrictive output impedance matching requirements. For frequencies below approximately 1 kHz, during the times at which the applied LF voltage equals zero, as seen in FIG. 5A, the LF plasma is extinguished and there is no LF plasma in the vacuum chamber. The LF plasma must then be re-ignited twice each cycle. By only operating in one voltage regime, LF sterilizers have simpler and more reliable electrical systems than do RF sterilizers. These electrical systems are easier to service and diagnose, thereby reducing the costs associated with repair. In addition, the higher peak plasma densities resulting from LF sterilizers likely result in increased dissociative recombination on the articles, thereby reducing the amount of residual reactive species remaining on the articles after the sterilization procedure.

Figures 6, 6A:
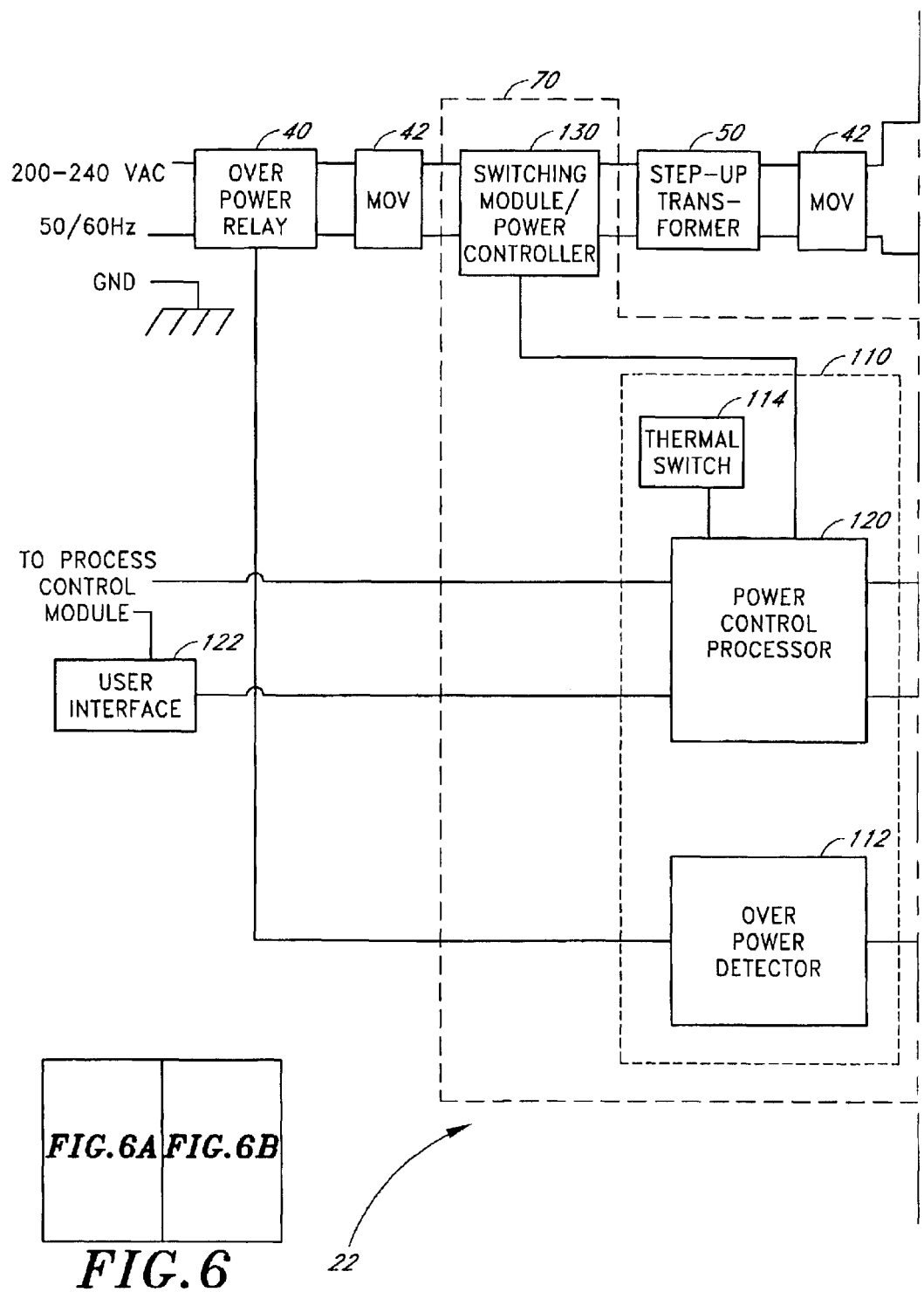
FIG. 6, which is broken into FIGS. 6A and 6B, schematically illustrates an embodiment of a low frequency power module comprising a switching module.
Figure 6B:
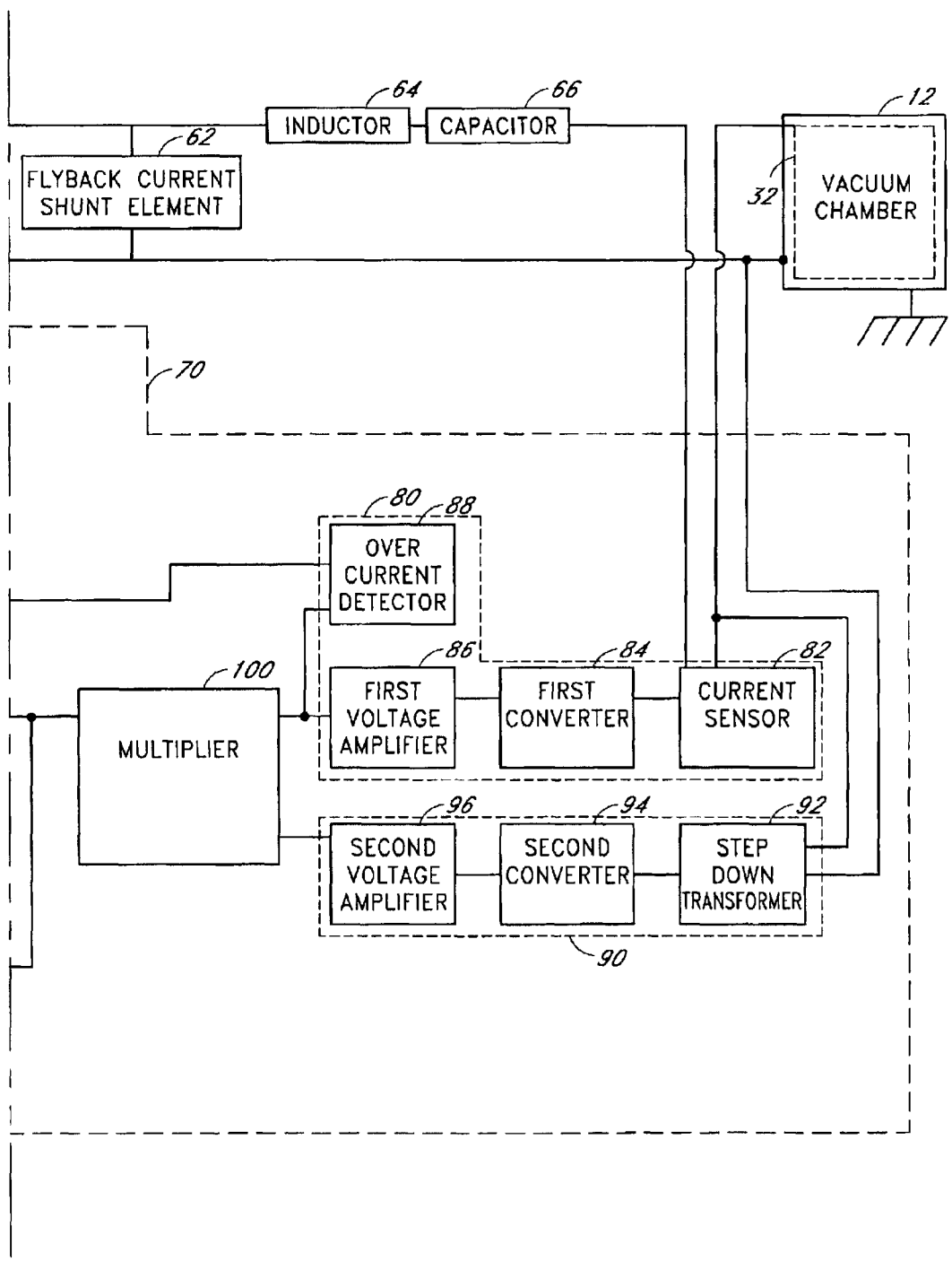

In certain embodiments, localized gas heating causes reductions of the plasma impedance, which then generate arcing or other plasma instabilities. This condition is more likely to occur where current densities are larger. However, this effect is reduced, and stability is increased, for frequencies higher than the 50/60 Hz of the incoming line voltage. As schematically illustrated in FIG. 6, which is broken into FIGS. 6a and 6b, certain embodiments of the LF power module 22 may also include a switching module 130 to provide higher frequencies by pulsating the LF power applied to the plasma. While FIG. 6 is based on the embodiment illustrated in FIG. 3, a switching module 130 can also be used by making a similar modification to the embodiment of FIG. 4. While FIG. 6 shows the switching module 130 inserted between the first MOV 42 and the step-up transformer 50, persons skilled in the art appreciate that other embodiments can have the switching module 130 at other locations within the LF power module 22.

Figure 7:
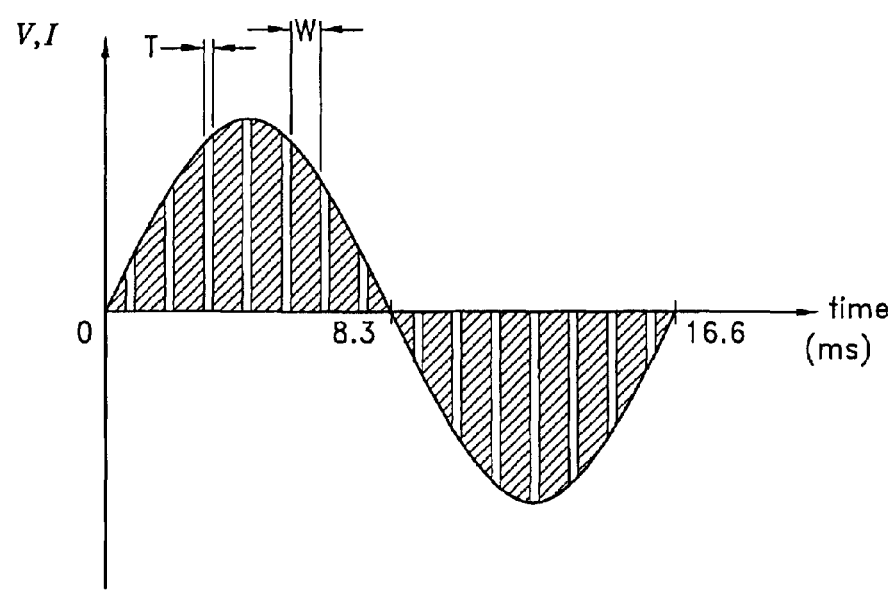
FIG. 7 schematically illustrates the output from a switching module which pulsates an incoming sinusoidal voltage with a frequency of 60 Hz to form a series of voltage pulses with widths W and spaced by times T.
Figure 8A:
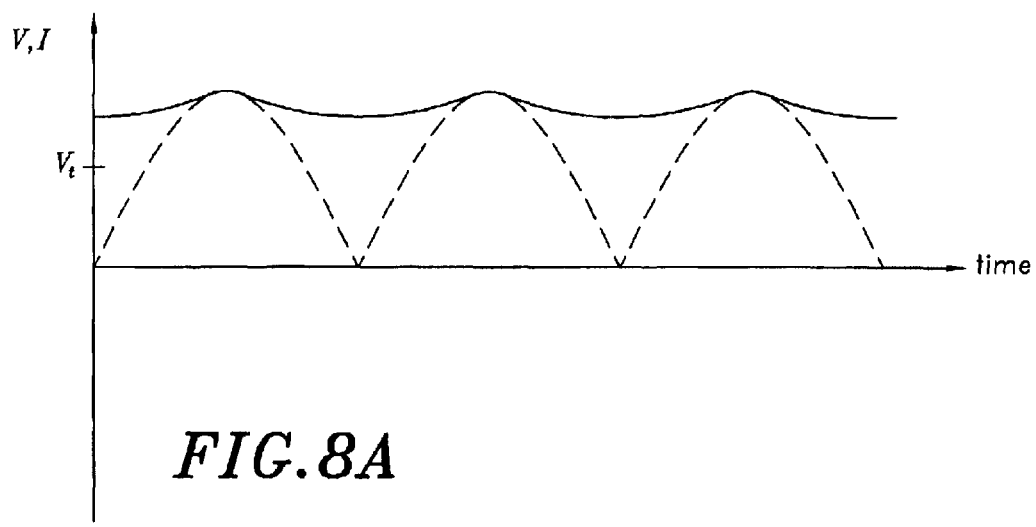
FIG. 8A schematically illustrates a rippled DC voltage generated by full-wave-rectifying and filtering the line voltage prior to pulsating the voltage via the switching module.

FIG. 7 schematically illustrates the output from a switching module 130 compatible with embodiments described herein. As shown in FIG. 7, an incoming sinusoidal voltage with a frequency of 60 Hz is pulsated by the switching module 130 to form a series of voltage pulses with widths W and spaced by times T. Persons skilled in the art appreciate that other waveforms may also be inputted into the switching module 130. For example, in order to minimize or eliminate periods in which the applied voltage is less than the threshold voltage $V_T$ required for plasma ignition, a rippled DC voltage can be generated by full-wave-rectifying and filtering the line voltage prior to pulsating the voltage via the switching module 130, as illustrated in FIG. 8a. In one embodiment, such a rippled DC voltage can be generated by inserting a AC-to-DC converter in the device schematically illustrated by FIG. 6 between the over power relay 40 and the MOV 42. In another embodiment, a power factor correction module can be used. An exemplary power factor correction module compatible with embodiments described herein is available as Part No. PFC-600 from RO Associates, Inc. of Sunnyvale, Calif. Persons skilled in the art can identify other embodiments which can generate such a rippled DC voltage.

Figure 8B:
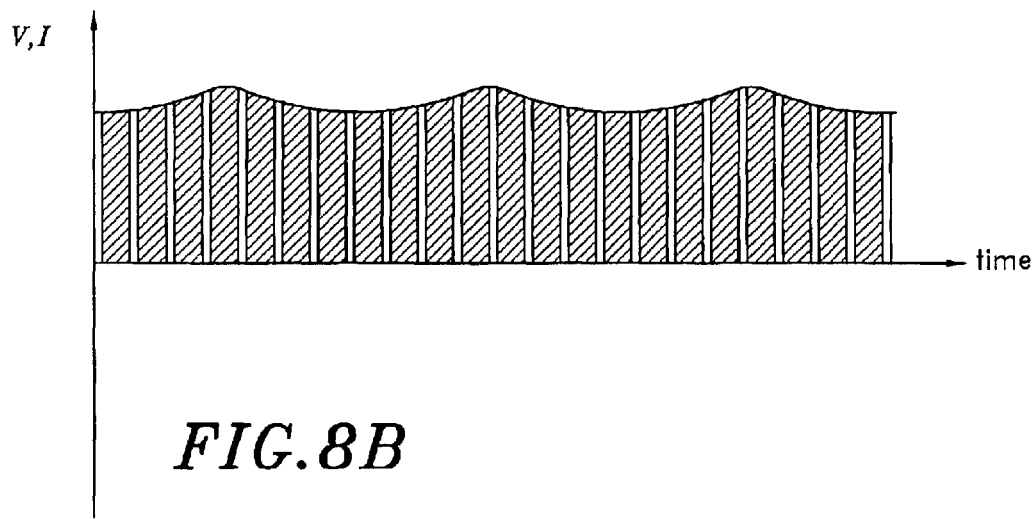
FIG. 8B schematically illustrates the rippled DC voltage of FIG. 8A after being pulsated by the switching module utilizing unipolar switching.
Figure 8C:
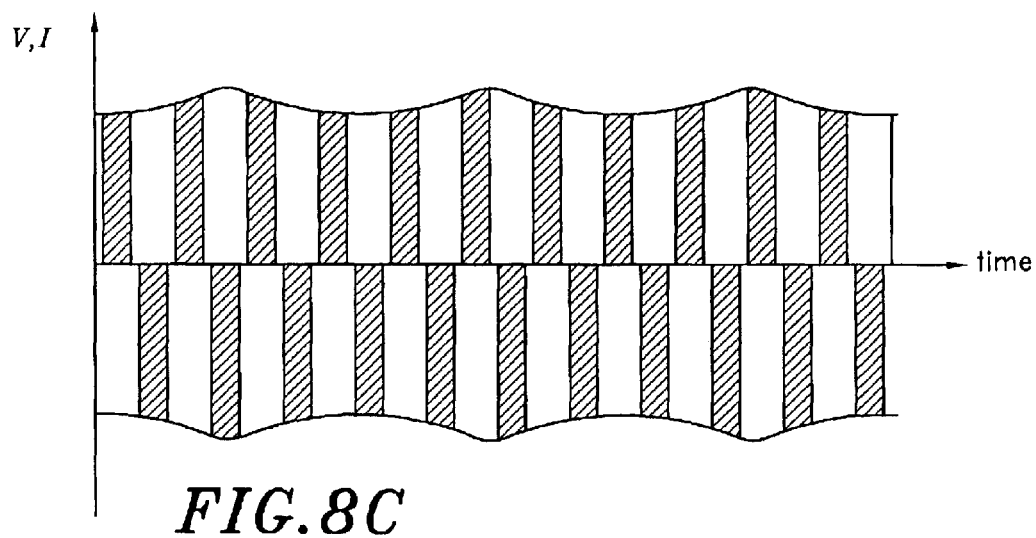
FIG. 8C schematically illustrates the rippled DC voltage of FIG. 8A after being pulsated by the switching module utilizing bipolar switching.
Figure 9:
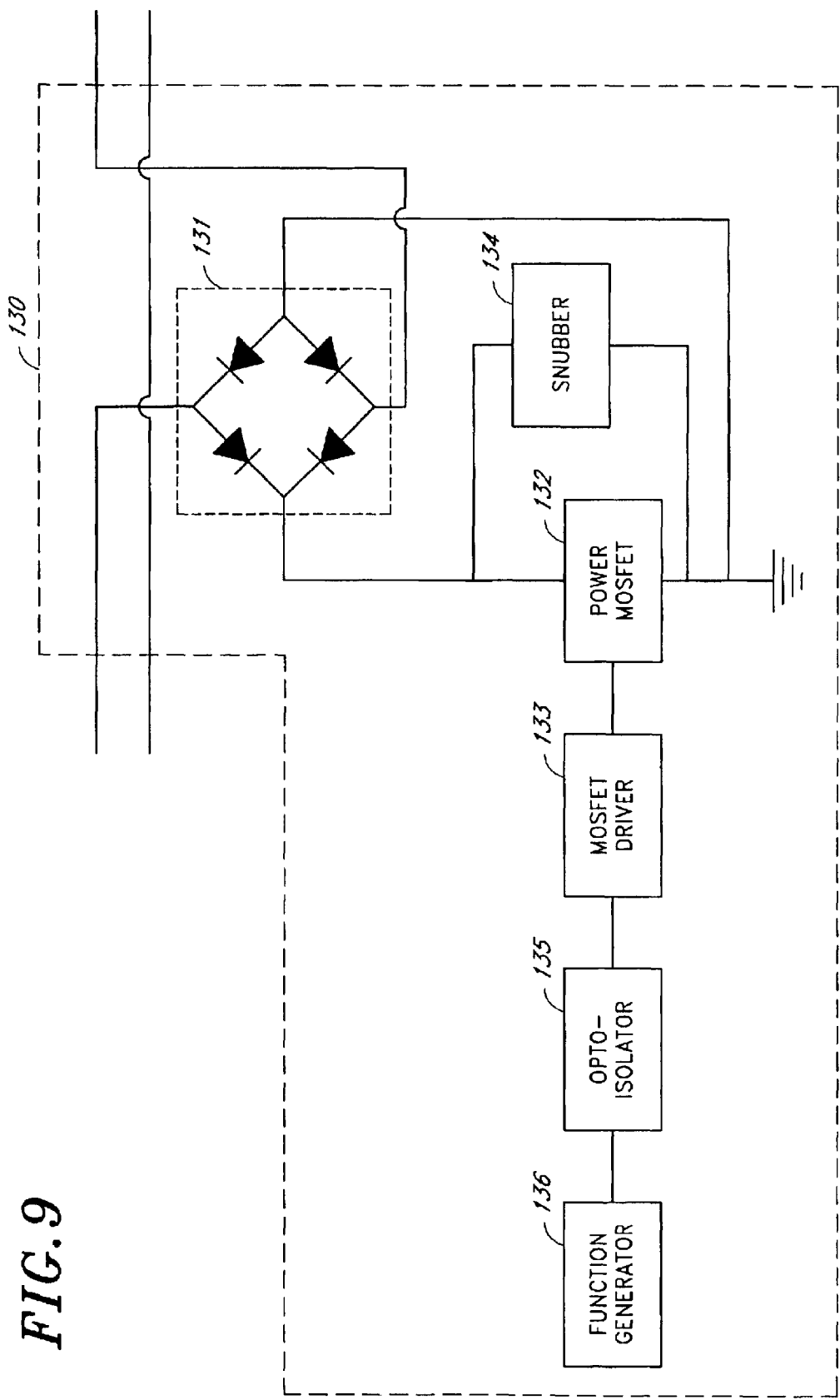
FIG. 9 schematically illustrates one embodiment of a switching module which generates a unipolar pulsation.

For illustrative purposes, the output of the switching module 130 illustrated in FIG. 7 has a frequency of approximately 1000 Hz. Persons skilled in the art appreciate that other frequencies are compatible with embodiments described herein. The output frequency of the switching module is preferably less than or equal to approximately 200 kHz (which includes DC voltages and currents), more preferably between approximately 1 kHz to 100 kHz, and most preferably between approximately 20 kHz to 50 kHz. In addition, the switching module 130 can be configured to provide an output with unipolar pulsation, as illustrated in FIG. 8b, or with bipolar pulsation, as illustrated in FIG. 8c. Bipolar pulsation reduces the possibility of electrode sputtering by the plasma and can provide a more stable plasma. FIG. 9 schematically illustrates one embodiment of a switching module 130 which generates a unipolar pulsation by utilizing a bridge rectifier 131, a power MOSFET 132, a MOSFET driver 133, a snubber 134, a opto-isolator 135, and a function generator 136. The snubber 134 is used to shunt the energy stored in the leakage inductance of the step-up transformer 50 so it does not damage the power MOSFET 132. An example of an opto-isolator 135 compatible with embodiments described herein is the 4N26 phototransistor optocoupler, sold by Texas Instruments of Dallas, Tex. An example of a power MOSFET 132 compatible with embodiments described herein is the "Super-247," serial number IRFPS37N50A, sold by International Rectifier of El Segundo, Calif. An example of a MOSFET driver 133 compatible with embodiments described herein is the SN75372 dual MOSFET driver, sold by Texas Instruments of Dallas, Tex.

In certain embodiments, such as that illustrated in FIG. 9, the LF power applied to the plasma can also be adjusted by the switching module 130 by adjusting pulse widths W or times T between pulses. In certain embodiments, the function generator 136 can be replaced by a pulse width modulation (PWM) controller that automatically controls the applied LF power. While the period (W+T) is the inverse of the selected pulsating frequency, the ratio of W/T can be varied to control the average LF power applied to the plasma. In such embodiments, the switching module 130 can receive appropriate signals from the power control processor 120 to appropriately select the pulse widths W and/or times T.

Figure 10:
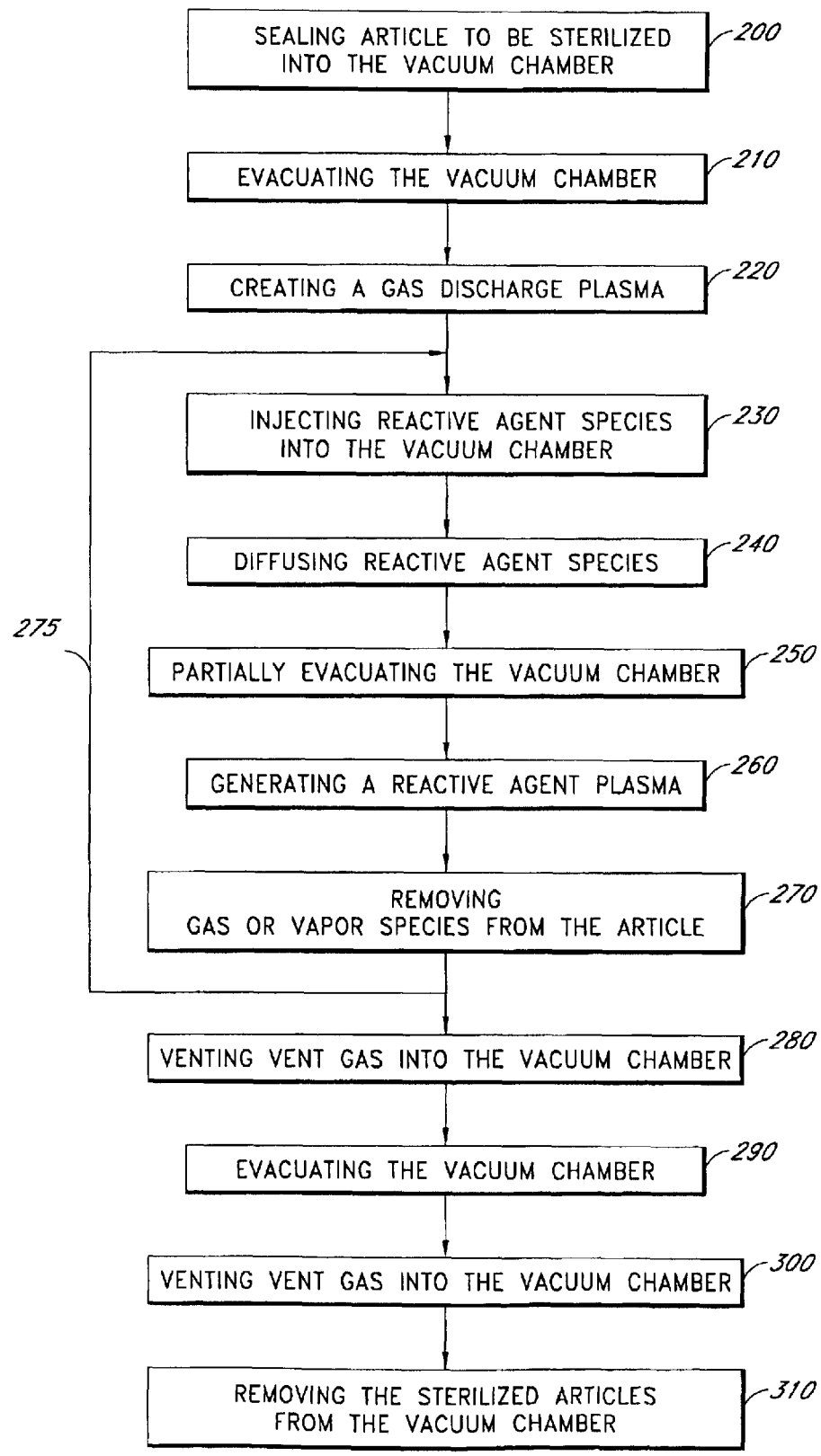
FIG. 10 schematically illustrates an embodiment of a method of sterilization.

FIG. 10 schematically illustrates a method of sterilization using the apparatus schematically illustrated in FIG. 1. The sterilization process shown in FIG. 10 is exemplary, and persons skilled in the art recognize that other processes are also compatible with embodiments described herein. Certain embodiments of the process of FIG. 10 begin by sealing 200 the article to be sterilized into the vacuum chamber 12. The vacuum chamber is then evacuated 210 by engaging the vacuum pump 14 and the vacuum valve 16 under the control of the process control module 30. The vacuum chamber 12 is preferably evacuated to a pressure of less than approximately 1320 Pa (10 Torr), more preferably between approximately 25 to 270 Pa (0.2 to 2 Torr), and most preferably between approximately 40 to 200 Pa (0.3 to 1.5 Torr).

In an exemplary process, upon reaching a desired pressure in the vacuum chamber 12, the process control module 30 signals the LF power module 22 to energize the electrode 32 within the vacuum chamber 12. By applying a LF voltage to the electrode 32, the LF power module 22 ionizes the residual gases in the vacuum chamber 12, thereby creating 220 a gas discharge LF plasma inside the vacuum chamber 12. This gas discharge LF plasma is formed from the residual gases in the vacuum chamber 12, which are primarily air and water vapor. Because this gas discharge LF plasma is created 220 before the reactive agent is injected into the vacuum chamber 12, this gas discharge LF plasma is typically called the "pre-injection" plasma. The vacuum valve 14 is controllably opened and closed to maintain a preset vacuum pressure during the pre-injection plasma step 220. The pre-injection plasma heats the surfaces inside the vacuum chamber 12, including the articles, thereby aiding the evaporation and removal of condensed water and other absorbed gases from the vacuum chamber 12 and the articles. A similar pre-injection plasma is described by Spencer, et al. in U.S. Pat. Nos. 5,656,238 and 6,060,019, which are incorporated by reference herein. In an exemplary process, the pre-injection plasma is turned off after approximately 0 to 60 minutes. Other embodiments do not include the creation of the pre-injection plasma, or use multiple pre-injection plasmas. In still other embodiments, the vacuum chamber 12 can be vented after the articles are exposed to the pre-injection plasma.

In certain embodiments of the process, upon reaching a desired chamber pressure, the vacuum valve 16 is closed, and the reactive agent valve 20 is opened under the control of the process control module 30, thereby injecting 230 reactive agent from the reactive agent source 18 into the vacuum chamber 12 via the reactive agent line 19. In certain embodiments, the reactive agent comprises hydrogen peroxide, which is injected in the form of a liquid which is then vaporized. The injected liquid contains preferably from about 3% to 60% by weight of hydrogen peroxide, more preferably from about 20% to 60% by weight of hydrogen peroxide, and most preferably from about 30% to 60% by weight of hydrogen peroxide. The concentration of hydrogen peroxide vapor in the vacuum chamber 12 may range from 0.125 to 20 mg of hydrogen peroxide per liter of chamber volume. The higher concentrations of hydrogen peroxide will result in shorter sterilization times. Air or inert gas such as argon, helium, nitrogen, neon, or xenon may be added to the chamber with the hydrogen peroxide to maintain the pressure in the vacuum chamber 12 at the desired level. This injection 230 of reactive agent may occur as one or more separate injections.

Due to this injection 230 of reactive agent, the chamber pressure of certain embodiments of the process rises to approximately 2000 Pa (15 Torr) or more. After approximately 6 minutes into the injection stage 230, the reactive agent is permitted to diffuse 240 completely and evenly throughout the vacuum chamber 12. After approximately 1–45 minutes of diffusing 240, the reactive agent is substantially in equilibrium inside the vacuum chamber 12. This diffusing 240 allows the reactive species to diffuse through the packaging material of the articles, and come into close proximity, if not contact, with the surfaces of the articles, thereby sterilizing the articles. In other embodiments, the diffusion of the reactive agent can be immediately followed by a vent of the vacuum chamber 12.

The vacuum chamber 12 is then partially evacuated 250 by pumping out a fraction of the reactive agent from the vacuum chamber 12 by controllably opening the vacuum valve 16 under the control of the process control module 30. Once the vacuum pressure within the vacuum chamber 12 has reached the desired pressure, the vacuum valve 16 is controllably adjusted to maintain the desired pressure, and the process control module 30 signals the LF power module 22 to energize the electrode 32 within the vacuum chamber 12. In certain embodiments in which the reactive agent comprises hydrogen peroxide, the pressure of the hydrogen peroxide in the vacuum chamber 12 is preferably less than approximately 1320 Pa (10 Torr), more preferably between approximately 25 and 270 Pa (0.2 to 2 Torr), and most preferably between approximately 40 and 200 Pa (0.3 to 1.5 Torr). By applying a LF voltage to the electrode 32, the LF power module 22 generates 260 a reactive agent LF plasma inside the vacuum chamber 12 by ionizing the reactive agent. The article is exposed to the reactive agent LF plasma for a controlled period of time. In certain embodiments, an additional cycle 275 is performed. Other embodiments may omit this additional cycle 275, or may include further cycles.

In both RF and LF plasmas, the components of the reactive agent plasma include dissociation species of the reactive agent and molecules of the reactive agent in excited electronic or vibrational states. For example, where the reactive agent comprises hydrogen peroxide as in certain embodiments, the reactive agent plasma likely includes charged particles such as electrons, ions, various free radicals (e.g., OH, $O_2H$), and neutral particles such as ground state $H_2O_2$ molecules and excited $H_2O_2$ molecules. Along with the ultraviolet radiation produced in the reactive agent plasma, these reactive agent species have the potential to kill spores and other microorganisms.

Once created, the charged particles of the reactive agent plasma are accelerated by the electric fields created in the vacuum chamber 12. Because of the fluid communication between the first region 31 and the second region 33, some fraction of the charged particles created in the first region 31 are accelerated to pass from the first region 31 to the second region 33 which contains the articles.

Charged particles passing from the first region 31 to the second region 33 have their trajectories and energies affected by the electric potential differential of the sheath regions between the plasma and the walls of the vacuum chamber 12 and the electrode 32. These sheath regions are created by all electron-ion plasmas in contact with material walls, due to charged particles impinging from the plasma onto the walls. Electrons, with their smaller mass and hence greater mobility, are lost from the plasma to the wall before the much heavier and less mobile ions, thereby creating an excessive negative charge density surrounding the walls and a corresponding voltage differential which equalizes the loss rates of the electrons and the ions. This voltage differential, or sheath voltage, accelerates electrons away from the wall surface, and accelerates positive ions toward the wall surface.

The sheath voltage varies for different plasma types, compositions, and methods of production. For RF plasmas, the sheath voltage is typically 40%–80% of the RF voltage applied to the electrode 32. For example, for a root-mean-squared (RMS) RF voltage of 140 $V_{rms}$ applied to the electrode 32 once the RF plasma is established, the corresponding sheath voltage is approximately 55–110 V. An ion entering the sheath region surrounding the electrode 32 will then be accelerated to an energy of 55–110 eV. This acceleration of positive ions by the sheath voltage is the basic principle behind semiconductor processing by RF plasmas.

As described above, for the LF plasmas of certain embodiments, the voltage applied to the electrode 32 may be equal to or greater than the ignition threshold voltage, which is typically 300 V. In addition, for LF plasmas, the sheath voltage is typically a higher percentage of the applied voltage than for RF plasmas, so the sheath voltage of certain embodiments is then much higher than the sheath voltage for an RF plasma system. This higher sheath voltage thereby accelerates the charged particles of the LF plasma to much higher energies. Therefore, because the charged particles are accelerated to higher energies, the charged particles of the LF plasma of certain embodiments travel farther and interact more with the articles than do the charged particles of RF plasma sterilizers.

Since the LF electric field changes polarity twice each cycle, the direction of the electric field acceleration on the charged particles reverses twice each cycle. For charged particles in the first region 31, this oscillation of the direction of the acceleration results in an oscillation of the position of the charged particles. However, because of the fluid communication between the first region 31 and the second region 33, some fraction of the charged particles are able to pass to the second region 33 containing the articles from the first region 31 before the direction of the electric field acceleration reverses.

The fraction of the charged particles created in the reactive agent LF plasma which enter the second region 33 is a function of the frequency of the applied electric field. The charged particles have two components to their motion— random thermal speed and drift motion due to the applied electric field. The thermal speed, measured by the temperature, is the larger of the two (typically approximately $10^7$–$10^8$ cm/sec for electrons), but it does not cause the charged particles to flow in any particular direction. Conversely, the drift speed is directed along the electric field, resulting in bulk flow of charged particles in or opposed to the direction of the applied electric field. The magnitude of the drift speed is approximately proportional to the magnitude of the applied electric field, and inversely proportional to the mass of the charged particle. In addition, the magnitude of the drift speed is dependent on the gas species and chamber pressure. For example, for typical operating parameters of gas discharge plasma sterilizers, including an average electric field magnitude of approximately 1 volt/cm, the drift speed for an electron formed in a gas discharge plasma is typically approximately $10^6$ cm/sec.

A charged particle enters the second region 33 containing the articles only if it reaches the second region 33 before the polarity of the applied electric field changes, which would reverse the acceleration of the charged particle away from the electrode 32. For example, for an applied RF electric field with a frequency of 13.56 MHz, the period of the electric field is approximately $7.4 \times 10^{-8}$ sec, so an electron only moves a distance of approximately $3.7 \times 10^{-3}$ cm during the half-cycle or half-period before the direction of the electric field changes and the electron is accelerated away from the electrode 32. Due to their much larger masses, ions move much less than do electrons. Where the first region 31 between the vacuum chamber 12 and the electrode 32 is approximately 2.54 cm wide, as in certain embodiments, only a fraction of the charged particles created by an RF plasma would actually reach the second region 33 containing the articles.

Conversely, for an applied LF electric field with a frequency of 60 Hz, the period of the electric field is approximately $16.7 \times 10^{-3}$ sec, so an electron can move approximately $8.35 \times 10^3$ cm before it is accelerated away from the electrode 32. Therefore, the use of LF voltages to create the plasma in the sterilization system 10 of certain embodiments results in more activity in the second region 33, as compared to a plasma generated using RF voltages. This higher activity in LF sterilizers likely contributes to the increased efficiency for the removal of residual reactive species from the sterilized articles as compared to RF sterilizers.

The plasma decay time, defined as a characteristic time for the plasma to be neutralized after power is no longer applied, provides an approximate demarcation between the LF and RF regimes. The plasma decay time is not known precisely, but it is estimated to be approximately $10^{-4}$–$10^{-3}$ sec for the plasma densities used in certain embodiments of the sterilizer system. This plasma decay time corresponds to the time a charged particle exists before it is neutralized by a collision with a surface or another plasma constituent, and is dependent on the plasma species generated and the geometries of the various components of the sterilization system 10. As described above, the LF regime is characterized by a plasma which is extinguished and re-ignited twice each cycle, i.e., the half-period of the applied LF voltage is greater than the plasma decay time. Therefore, the sterilization system 10 is continually run at an applied voltage above the ignition threshold voltage of the plasma in order to re-ignite the plasma. The estimated approximate range of plasma decay times of $10^{-4}$–$10^{-3}$ sec for many of the plasmas compatible with embodiments described herein then translates to an upper limit on the low frequency regime of approximately 1–10 kHz. However, under certain circumstances, higher frequencies can be tolerated.

Alternatively, the upper limit of the low frequency regime may be defined as the frequency at which the electron drift speed is too slow for an electron to traverse the 2.54-cm-wide first region 31 during a half-period of the applied LF voltage. Under typical operating geometries, this upper limit of the low frequency regime would be approximately 200 kHz. For other geometries, the upper limit of the low frequency regime can be correspondingly different.

In certain embodiments of the method, the LF power module 22 remains energized for approximately 2–15 minutes, during which the plasma removes excess residual reactive species present on surfaces within the vacuum chamber 12, including on the articles. There is a brief rise of the vacuum pressure upon generating 260 the plasma, however, the majority of the residual removal step 270 is conducted at an approximately constant vacuum pressure of 50 to 70 Pa (0.4 to 0.5 Torr). The residual removal step 270 is ended by the process control module 30, which turns off the LF power module 22, thereby quenching the plasma.

After the residual removal step 270, the vacuum chamber 12 is vented 280 by the process control module 30 which opens the vent valve 28, thereby letting in vent gas from the vent 26 through the vent line 27 and the vent valve 28. In certain embodiments of the process, the vacuum chamber 12 is then evacuated 290 to a pressure of approximately 40 to 105 Pa (0.3 to 0.8 Torr) to remove any remaining reactive agent which may be present in the vacuum chamber 12. The vacuum chamber 12 is then vented again 300 to atmospheric pressure, and the sterilized articles are then removed 310 from the vacuum chamber 12.

The LF plasma provides a reduction of the amount of residual reactive agent molecules remaining on the articles after the sterilization procedure is complete. Where the reactive agent comprises hydrogen peroxide, the amount of residual hydrogen peroxide remaining on the sterilized articles is preferably less than approximately 8000 ppm, more preferably less than approximately 5000 ppm, and most preferably less than approximately 3000 ppm. In a comparison of the amount of residual hydrogen peroxide remaining after a LF plasma sterilization as compared to a RF plasma sterilization, nine polyurethane test samples were exposed to hydrogen peroxide during a simulated sterilization cycle in both a LF sterilizer and a RF sterilizer. Each sample was prepared by washing with Manuklenz® and drying prior to sterilization to avoid any cross contamination. The nine samples were then distributed uniformly across the top shelf of a standard industrial rack.

A full LF sterilization cycle, which matched nearly exactly the conditions of a standard RF sterilizer cycle, was used to perform the comparison. The full LF sterilization cycle included a 20-minute exposure to a pre-injection plasma, a first 6-minute hydrogen peroxide injection, a vent to atmosphere, a 2-minute diffusion, a first 2-minute post-injection plasma, a second 6-minute hydrogen peroxide injection, a vent to atmosphere, a 2-minute diffusion, a second 2-minute post-injection plasma, and a vent to atmosphere. Two full LF sterilization cycles were performed and compared to two full RF sterilization cycles. As seen in Table 1, all parameters other than the post-injection plasma power were maintained as constant as possible from run to run.

Table 1

TABLE 1

|  | LF Run 1 | LF Run 2 | RF Run 1 | RF Run 2 |
|---|---|---|---|---|
| Pre-injection plasma power | 727 W | 779 W | 751 W | 752 W |
| First post-injection plasma power | 783 W | 874 W | 757 W | 756 W |
| Second post-injection plasma power | 755 W | 893 W | 758 W | 758 W |
| Chamber temp. | 45° C. nom. | 45° C. nom. | 45° C. nom. | 45° C. nom. |
| Injection system temp. | 65–75° C. | 65–75° C. | 65–75° C. | 65–75° C. |
| $H_2O_2$ concentration | 17 mg/l | 17 mg/l | 17 mg/l | 17 mg/l |
| Chamber pressure during plasma | 50 Pa (0.4 Torr) | 50 Pa (0.4 Torr) | 50 Pa (0.4 Torr) | 50 Pa (0.4 Torr) |

Variations in the pre-plasma power were ±3.5%, so the sample temperature was approximately constant from run to run. The samples were then removed and the residual analysis was performed.

The LF sterilizer used to generate the LF plasma was operated at 60 Hz, and with an inductor of 500 mH and a capacitor of 13.6 μF. LF plasma power was determined by multiplying the voltage across the LF plasma by the current, then averaging on an oscilloscope. The fluctuation level of the LF power was approximately 10%. Table 2 illustrates the results of the comparison.

Table 2

TABLE 2

|  | LF Run 1 | LF Run 2 | RF Run 1 | RF Run 2 |
|---|---|---|---|---|
| Average post-injection plasma power | 769 W | 884 W | 757 W | 757 W |
| $H_2O_2$ residuals (ppm) | 1973 ± 144 | 1864 ± 75 | 2682 ± 317 | 2510 ± 203 |

Exposure to a LF post-injection plasma reduced the residual reactive species more effectively than did exposure to a RF post-injection plasma of comparable power. LF Run 1 had approximately 23% less residual hydrogen peroxide than either RF Run 1 or RF Run 2, even though all had approximately the same post-injection plasma power. The LF processes therefore resulted in less residual hydrogen peroxide than did the corresponding RF process.

The comparison of the two LF sterilization cycles illustrates that increased plasma power results in a reduction of the hydrogen peroxide residuals. Furthermore, the variation between samples, as indicated by the standard deviation of the residual measurements, was significantly reduced in the LF process, thereby indicating an increased uniformity as compared to the RF process.

Figure 11:
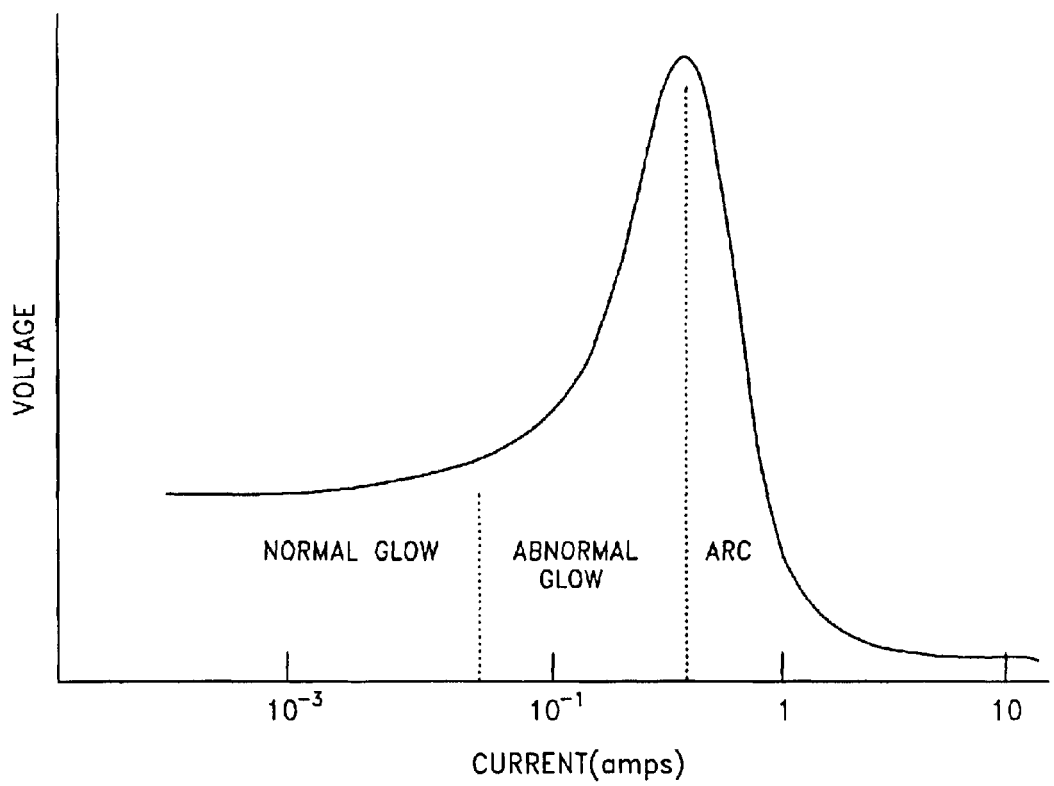
FIG. 11 schematically illustrates three operation regions of plasma discharge systems.

FIG. 11 schematically illustrates three operation regions of plasma discharge systems. The current levels dividing the regions from one another in FIG. 11 are only approximate, with the actual current levels dependent on various plasma parameters. In the normal glow region, corresponding to low currents, the discharge does not cover the entire electrode surface and the discharge current is determined by the resistance of the external circuitry. Lowering the resistance of the external circuitry will cause the discharge to expand to cover more of the electrode surface with a corresponding increase in the discharge current. Once the entire electrode surface is covered by the discharge, the discharge current can only be increased by increasing the applied voltage. This region is the abnormal glow region. Examples of plasma discharge systems which operate in the abnormal glow region include, but are not limited to, sterilization systems and semiconductor wafer fabrication systems.

The discharge transitions from the abnormal glow region to the arc region at some value of the discharge current. This transition is accompanied by a contraction of the discharge from a diffuse glowing discharge to a bright, filamentous discharge including thermionic emission from hot spots of the electrodes. The arc region is characterized by a negative resistance whereby the discharge can run to ever higher currents. The discharge current of the arc region is typically stabilized by a ballast that regulates the discharge current externally. Examples of plasma discharge systems which operate in the arc region include, but are not limited to, electrosurgical systems and plasma cutting systems.

To maintain the plasma within the abnormal glow region and to control the power dissipated by the plasma, prior art systems have utilized various power feedback control systems. U.S. Pat. No. 5,175,472 issued to Johnson, Jr. et al. describes an RF plasma power monitor to maintain plasma power at a preset level irrespective of impedance fluctuations and reflections. This RF plasma power monitor utilizes various analog pre-processing elements (including RMS converters, zero cross detectors, and frequency down-converters, and a data processor) prior to analog-to-digital conversion. U.S. Pat. No. 5,861,752 issued to Klick describes a feedback system for controlling unsymmetrical RF low-pressure plasmas by monitoring the discharge current to ground. U.S. Pat. No. 6,383,554 issued to Chang, et al. describes a feedback system for an RF plasma system which monitors plasma density using a heterodyne millimeter wave interferometer.

Figure 12:
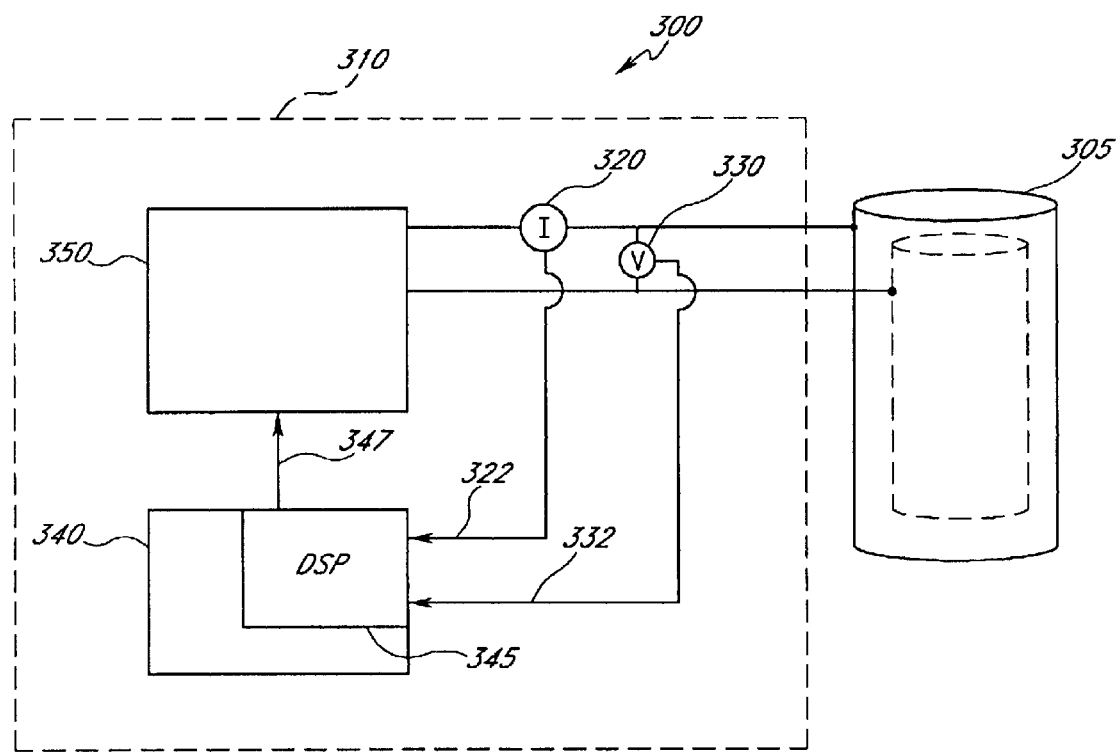
FIG. 12 schematically illustrates a sterilization system in accordance with embodiments described herein.

FIG. 12 schematically illustrates a sterilization system 300 in accordance with embodiments described herein. The sterilization system 300 applies power to a plasma within a chamber 305 to remove gas or vapor species from an article. The sterilization system 300 comprises a power feedback control system 310 for controlling the power applied to the plasma. The power feedback control system 310 comprises a current monitor 320 adapted to produce a first signal 322 indicative of a current applied to the plasma within the chamber 305. The power feedback control system 310 further comprises a voltage monitor 330 adapted to produce a second signal 332 indicative of a voltage applied to the plasma within the chamber 305. The power feedback control system 310 further comprises a power control module 340 comprising a programmable digital signal processor (DSP) 345. The DSP 345 is adapted to receive and process the first signal 322 and the second signal 332 by multiplying the current and the voltage and producing a third signal 347 indicative of the product of the current and the voltage. The power feedback control system 310 further comprises a plasma generator 350 coupled to the power control module 340. The plasma generator 350 is adapted to adjust, in response to the third signal 347, the power applied to the plasma within the chamber 305.

The plasma generator 350 of certain embodiments comprises power measurement and feedback control mechanisms to deliver constant power to the plasma. Power control can be achieved by amplitude modulation (FIG. 5B), pulse width modulation (FIGS. 5A, 7, 8B, and 8C), or frequency modulation. In certain embodiments, the plasma generator 350 is coupled to an external power source and comprises an over power relay, a pair of metal oxide varistors, and a step-up transformer, as schematically illustrated in FIGS. 3 and 4. In other embodiments, the plasma generator 350 further comprises a flyback current shunt element, an inductor, and a capacitor, as schematically illustrated in FIG. 3. In still other embodiments, the plasma generator 350 comprises a switching module as schematically illustrated in FIGS. 6 and 9.

In certain embodiments described herein, the plasma of the sterilization system 300 is a non-equilibrium plasma in the abnormal glow region of FIG. 11. To maintain the plasma within the abnormal glow region and to control the power dissipated by the plasma, certain embodiments utilize the DSP 345. For example, the DSP 345 can be programmed to modulate the magnitude of the applied voltage, or to modulate the time the voltage is applied, so as to maintain a predetermined average power value. Other embodiments can use the DSP 345 to control other parameters of the sterilization system 300 besides power. In certain embodiments, the DSP 345 is programmable to monitor plasma peak-to-peak voltages from approximately 0.1 kV to approximately 20 kV on a time frame between approximately 10 nanoseconds to approximately 10 milliseconds. In certain embodiments, the DSP 345 is programmable to monitor plasma peak-to-peak currents from approximately 0.01 A to approximately 100 A on a time frame between approximately 10 nanoseconds to approximately 10 milliseconds. An example of a commercially available DSP compatible with embodiments described herein is DSP series TMS320C6X from Texas Instruments of Dallas, Tex.

Generation of non-equilibrium plasmas in a chamber that contains residual gas or vapor compounds is facilitated by precise and rapid control of the plasma power, which can be provided by utilizing the DSP 345. The stability of the plasma is affected by various parameters such as the voltage applied to the plasma, the current conducted through the plasma, the plasma impedance, temperature, pressure, and the type of gas or vapor compounds. Because sterilization systems are typically used for a wide variety of articles to be sterilized, the loads of sterilization systems can vary significantly from cycle to cycle or from hospital to hospital. Conversely, the loads of semiconductor wafer fabrication systems are typically unchanging from load to load or from site to site because the wafers are generally the same. In addition, the load of a sterilization system can change during the course of processing due to the changing amount of sterilant or other constituents of the atmosphere within the sterilization system chamber. By using the programmable DSP 345 as described herein, the sterilization system 300 can respond to various parameters which vary from load to load, or which vary during processing of a load, thereby making the sterilization system 300 load-independent. This use of the programmable DSP 345 also provides speed and accuracy in the monitoring and control of the plasma which is unavailable in prior art systems.

In addition, the DSP 345 of certain embodiments is programmed to identify plasma instabilities in response to the monitored parameters and to respond to the plasma instability accordingly. Such a DSP 345 identifies plasma instabilities by monitoring the plasma voltage, plasma current, or plasma impedance (the calculated voltage divided by the current). For example, if the voltage decreases while the current increases abruptly, the DSP 345 would identify this instability and respond with a corrective action.

Figure 13:
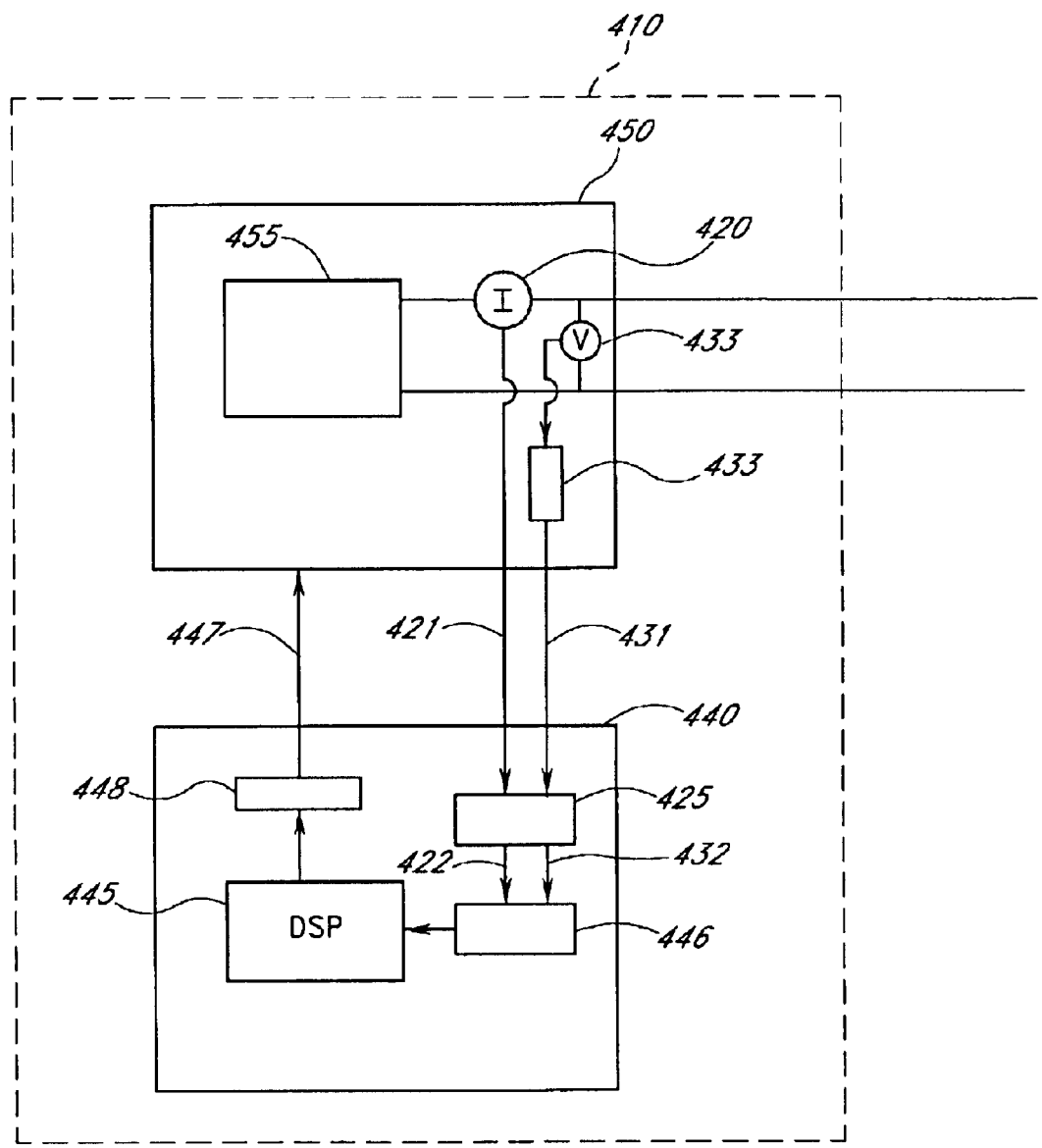
FIG. 13 schematically illustrates another power feedback control system in accordance with embodiments described herein.

FIG. 13 schematically illustrates another power feedback control system 410 in accordance with embodiments described herein. Both the current monitor 420 and the voltage monitor 430 are contained within the plasma generator 450 which comprises an output transformer 455. Typically, the output transformer 455 is custom designed for a particular application. In certain embodiments, the current monitor 420 comprises a current sense transformer that generates an analog current signal 421 which is converted to a digital current signal 422 by a high-speed, synchronous analog-to-digital converter 425 of the power control module 440. Examples of analog-to-digital converters compatible with embodiments described herein include ADS2807 and ADS5204, both available from Texas Instruments of Dallas, Tex. In certain embodiments, the voltage monitor 430 senses the voltage through a single turn on the output transformer 455 and generates an analog voltage signal 431 which is voltage divided by a voltage divider 433 and converted to a digital voltage signal 432 by the analog-to-converter 425.

In certain embodiments, the power control module 440 comprises a buffer 446 which stores the digital current signal 422 and the digital voltage signal 432 while awaiting further instructions from the DSP 445. The digital current signal 422 and the digital voltage signal 432 can be simultaneously or sequentially retrieved by the DSP 445, and are used to calculate the power applied to the plasma.

In certain embodiments, the DSP 445 multiplies the instantaneous current ($I_{instant}$) and the instantaneous voltage ($V_{instant}$) to calculate an instantaneous power ($P_{instant}$). The DSP 445 of certain embodiments also calculates an average power ($P_{ave}$) by averaging $P_{instant}$ over predetermined window. The value of $P_{ave}$ can be used to provide information regarding the pulse-to-pulse variations of the reactive power applied to the plasma.

In other embodiments, the DSP 445 uses $I_{instant}$ and $V_{instant}$ to simultaneously calculate root-mean-square (RMS) values for both the plasma current ($I_{RMS}$) and plasma voltage ($V_{RMS}$). Calculation of these RMS values is made using at least one full cycle of the applied current and voltage. These RMS values are then inputted into a power calculation algorithm by the DSP 445 to calculate the average power $P_{ave}$ over a predetermined number of waveform periods.

In still other embodiments, the DSP 445 calculates $P_{ave}$ using both algorithms described above. While the values of $P_{ave}$ should be identical from both algorithms, differences can result from shifts between $V_{instant}$ and $I_{instant}$ thereby providing information regarding the load impedance and the reactive power. The term "reactive power" as used herein refers to the flow of energy stored in the reactive components of the load.

In certain embodiments, the DSP 445 is programmable to monitor plasma impedance. Plasma impedance is defined by the ratio of the applied voltage and the applied current, and is a function of various parameters of the load. In such embodiments, the DSP 445 can respond to changes of the plasma impedance by making adjustments in the applied power. The plasma impedance can be monitored from approximately 0.5 ohms to approximately 200 ohms on a time frame between approximately 10 nanoseconds to approximately 1000 nanoseconds.

In certain embodiments, the DSP 445 generates a power signal 447 indicative of the power applied to the plasma and the power signal 447 is transmitted to the power generator 450. In certain such embodiments, to provide a signal compatible with the power generator 450, the power signal 447 is scaled by a constant factor and is converted to an analog waveform through a digital-to-analog converter 448. Examples of digital-to-analog converters compatible with embodiments described herein include THS5651A and THS55671A available from Texas Instruments of Dallas, Tex.

In certain embodiments in which the power generator 450 comprises a pulse width modulator, the power generator 450 responds to the power signal 447 by adjusting the widths of the applied voltage and current pulses to maintain a predetermined applied power. Examples of pulse width modulators compatible with embodiments described herein include SG3526N available from Microsemi Corp. of Irvine, Calif. The power generator 450 of other embodiments can respond to the power signal 447 in other ways (e.g., adjusting the applied magnitudes, waveforms, or frequencies) to maintain a predetermined applied power.

Figure 14:
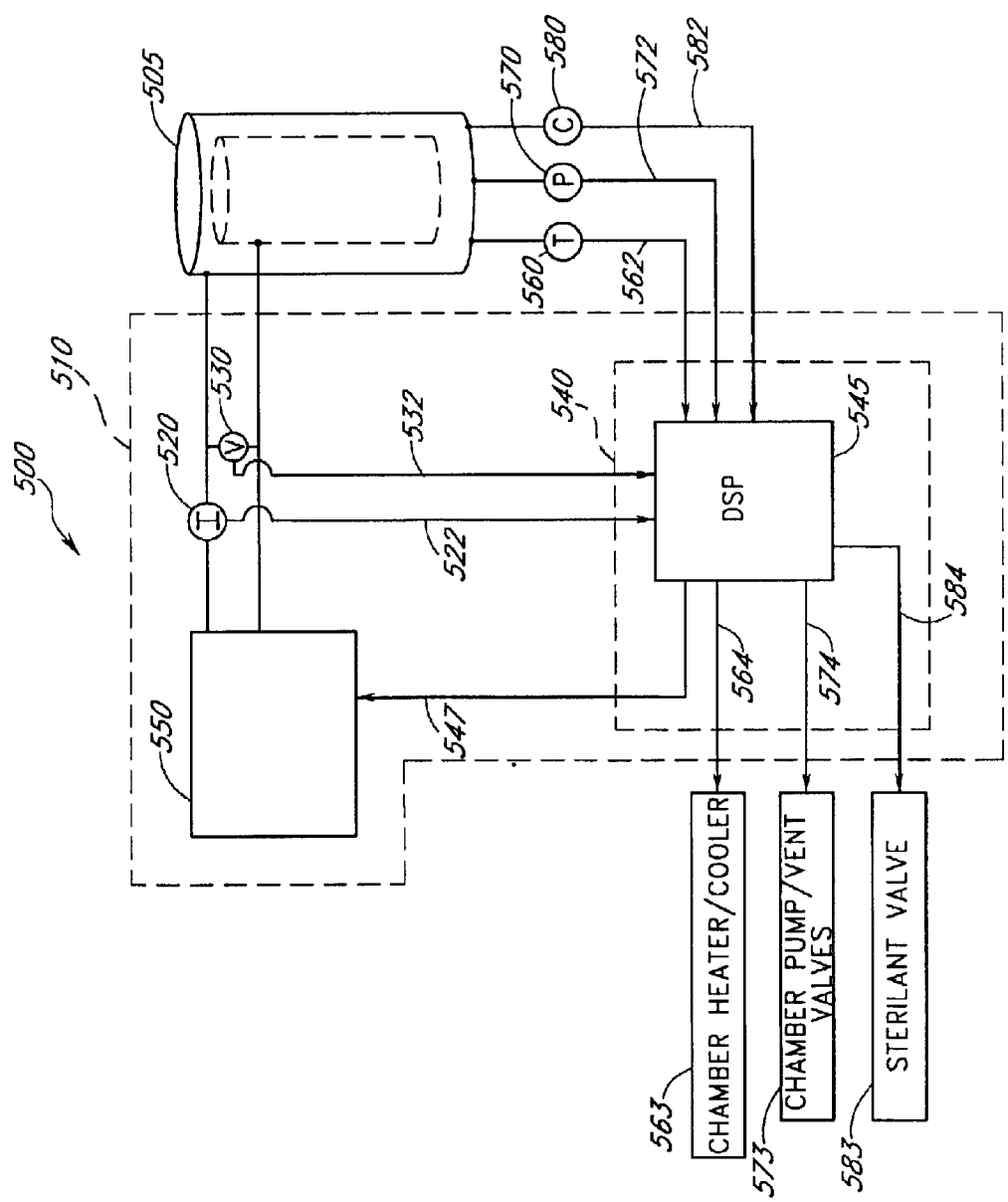
FIG. 14 schematically illustrates another sterilization system in accordance with embodiments described herein.

FIG. 14 schematically illustrates another sterilization system 500 in accordance with embodiments described herein. The sterilization system 500 applies power to a plasma within a chamber 505 to remove gas or vapor species from an article. The sterilization system 500 comprises a power feedback control system 510 which comprises a current monitor 520 adapted to produce a first signal 522 indicative of a current applied to the plasma within the chamber 505. The power feedback control system 510 further comprises a voltage monitor 530 adapted to produce a second signal 532 indicative of a voltage applied to the plasma within the chamber 505. The power feedback control system 510 further comprises a power control module 540 comprising a programmable DSP 545 adapted to produce a third signal 547 in response to the first signal 522 and the second signal 532. The power feedback control system 510 further comprises a plasma generator 550 coupled to the power control module 540 and adapted to adjust, in response to the third signal 547, the power applied to the plasma within the chamber 505.

Because the plasma power changes nonlinearly with changes in the load (e.g., due to changes in the chamber pressure, gas composition, or chamber temperature), the DSP 545 of certain embodiments is adapted to respond to signals from peripheral monitoring devices which monitor these parameters. For example, the sterilization system 500 schematically illustrated in FIG. 14 further comprises a temperature monitor 560 (e.g., thermocouple, thermistor, or fiber optic temperature sensor) adapted to produce an electrical signal 562 indicative of the chamber temperature. The sterilization system 500 further comprises a pressure monitor 570 (e.g., parallel plate capacitor sensor) adapted to produce an electrical signal 572 indicative of the chamber pressure. The sterilization system 500 further comprises a concentration monitor 580 adapted to produce an electrical signal 582 indicative of the sterilant concentration within the chamber 505. Examples of concentration monitor 580 compatible with embodiments described herein include the ultraviolet absorption monitor described in U.S. Pat. No. 6,269,680, which is incorporated herein in its entirety. In certain embodiments, the signals from these peripheral monitoring devices are converted using analog-to-digital converters and held in buffers until retrieved by the DSP 545. Other sterilization systems in accordance with other embodiments include only a subset of these peripheral monitoring devices, or include other peripheral monitoring devices.

In certain such embodiments, the DSP 545 is adapted to receive the signals from the peripheral monitoring devices and to respond by adjusting the power applied to the plasma by adjusting the third signal 547 transmitted to the plasma generator 550. For example, the DSP 545 can adjust the power in response to pressure changes within the chamber 505 which affect the plasma power. In certain embodiments, the DSP 545 responds to the nonlinear effects by adjusting the algorithms used to calculate the power applied to the plasma. For example, during the first minute of plasma operation, the plasma impedance changes rapidly and nonlinearly. Under such conditions, reaction time is more important than signal-to-noise, so the DSP 545 shortens the reaction time by reducing the number of waveform periods averaged to calculate $P_{ave}$. In certain embodiments, the reaction time is preferably less than approximately 10 seconds, more preferably less than approximately 5 seconds, and most preferably less than approximately 2 seconds. In certain embodiments, the DSP 545 is programmable to regulate the plasma power to be within approximately 5% of the predetermined average power value, while in other embodiments, the DSP 545 is programmable to regulate the plasma power to be within approximately 0.1% of the predetermined average power value.

In still other embodiments, the DSP 545 is coupled to various peripheral control devices which adjust the parameters monitored by the peripheral monitoring devices. In certain embodiments, the DSP 545 maintains the parameters at predetermined values which are either predefined by the sterilization system 500 or are user-defined.

For example, the sterilization system 500 schematically illustrated in FIG. 14 has a DSP 545 coupled to a chamber heater/cooler 563 (e.g., thermoelectric heater/cooler) which responds to a temperature control signal 564 generated by the DSP 545 to control the chamber temperature. The DSP 545 is also coupled to various chamber pump/vent valves 573 which respond to pressure control signals 574 generated by the DSP 545 to control the chamber pressure. The DSP 545 is also coupled to a sterilant valve 583 (e.g., mass flow controller) which responds to a concentration control signal 584 generated by the DSP 545 to control the concentration of the sterilant in the chamber 505. In certain embodiments, the control signals from the DSP 545 are converted by a digital-to-analog converter before being transmitted to the peripheral control device. Other sterilization systems in accordance with other embodiments include only a subset of these peripheral control devices, or include other peripheral control devices.

The sterilization system 500 of certain embodiments ignites the plasma first by open loop power control, followed by closed loop power control. Open loop power control comprises fixing the pulse widths at a predefined pulse width and continuing to apply the voltage pulses until the plasma ignites. In certain embodiments, the predefined pulse width is between approximately 0.6 μsec and approximately 2 μsec. Open loop power control can also comprise changing the magnitude of the voltage pulses or some other system parameter (e.g., chamber pressure) until the plasma is ignited. Open loop power control is useful to limit the applied current in a pulse during the ignition stage where applied voltages are high. Voltages during the ignition stage are typically hundreds to thousands of volts, depending on the configuration of the plasma system. As the voltage decreases to the nominal operating voltage, the fixed pulse width allows the applied current to approach to the nominal operating value during ignition. In certain embodiments, the DSP 545 is programmable to detect plasma ignition on a time frame between approximately 10 nanoseconds to approximately 100 milliseconds.

Once the DSP 545 detects plasma ignition by detecting a power value above a predetermined average power value (e.g., approximately 100–150 W) and an applied current above a predetermined current threshold, the DSP 545 transitions to closed loop power control. In closed loop power control, the DSP 545 utilizes the detected plasma power to generate the feedback signal. In certain embodiments, this feedback signal is transmitted to the plasma generator 550 to vary the pulse widths to achieve a predetermined average power value.

The DSP 545 of certain embodiments is programmable to provide open-circuit protection and to attempt to reestablish the plasma upon detection of the open-circuit conditions. Open-circuit conditions are characterized by small currents and large voltages. Causes of open-circuit conditions include, but are not limited to, abrupt changes in the chamber pressure which cause the plasma to extinguish, chamber pressures which are too high or too low, excessive sterilant concentrations, excessive water concentrations, or loose electrical connections.

The DSP 545 of certain embodiments is programmable to provide short-circuit protection by terminating the plasma generation upon detection of short-circuit conditions. Short-circuit conditions are characterized by large currents and small voltages and can cause damage to the electronics of the sterilization system 500 if the large currents are allowed to continue too long. Causes of short-circuit conditions include, but are not limited to, an arc discharge (sometimes referred to as "filamentation") between the electrodes or a direct electrical connection between the electrodes. In certain embodiments, the DSP 545 compares the applied plasma current values to a predetermined threshold value indicative of a short-circuit condition. When the applied plasma current exceeds this predetermined threshold value, the DSP 545 signals the power generator 550 to turn off the applied plasma power prior to the next applied pulse. After turning off the applied plasma power, the sterilization system 500 attempts to reignite the plasma, as described above.

In contrast to prior art systems which monitor an average power applied to the plasma over a period of time, certain embodiments of the sterilization system 500 described herein provide "real-time" monitoring and control of the power applied to the plasma. For example, U.S. Pat. No. 5,175,472 issued to Johnson, Jr. et al. describes an RF plasma power monitor that utilizes "sample and hold" frequency converters to downconvert the frequency of the applied RF current and voltage to a frequency which can be monitored by subsequent modules of the power monitor. Such downconversion is effectively an averaging of the applied power over a number of periods of the RF waveform. The power monitor described by this prior art reference also uses various analog mathematical pre-processing modules, such as a multiplier, to process the averaged current and voltage signals prior to converting these signals into digital form. Such systems do not provide "real-time" monitoring and control because they are only responsive to changes of the plasma power on time scales longer than the inverse of the waveform frequency.

Conversely, in certain embodiments described herein, the sterilization system 500 provides intra-pulse monitoring and control of the power applied to the plasma. In certain such embodiments, the DSP 545 provides intra-pulse monitoring by monitoring changes of the instantaneous plasma impedance (i.e., the ratio of $V_{instant}$-to-$I_{instant}$) within an applied power pulse. For example, the DSP 545 disables the plasma generator 550 prior to the start of the next pulse if the instantaneous plasma impedance indicates that the short-circuit condition exists. In certain embodiments, the plasma generator 550 is disabled during the pulse in which the short-circuit condition is detected. In this way, the sterilization system 500 provides "real-time" intra-pulse protection of the electronics in the event of a short circuit.

In certain embodiments in which the power has a waveform frequency, the power control module 550 preferably has a processing speed faster than the inverse of the waveform frequency, and more preferably has a processing speed faster than one-half of the inverse of the waveform frequency. In certain embodiments in which a power wavetrain is applied to the plasma, the power wavetrain comprises a plurality of power pulses having a characteristic pulse period. In certain such embodiments, the power applied to the plasma is adjusted on a time scale shorter than the characteristic pulse period. The sterilization system 500 of certain embodiments provides intra-pulse monitoring and control during the entire power wavetrain.

In certain other embodiments, the DSP 545 provides inter-pulse monitoring by monitoring the plasma impedance over numerous pulses (i.e., the ratio of $V_{RMS}$-to-$I_{RMS}$). In addition, the DSP 545 of certain embodiments is programmed to recognize the small current and large voltage values of the open-circuit condition and to correlate these values with abnormalities in other system parameters (e.g., pressure or sterilant concentration). Where appropriate, the DSP 545 is programmed to reestablish the plasma to full power by stabilizing the system parameters. In certain embodiments, where the open-circuit conditions are detected to be correlated with abrupt changes of the chamber pressure, the DSP 545 will attempt to control the chamber pressure by transmitting appropriate signals to the chamber pump/vent valves 573.

In certain embodiments, unwanted noise in the first signal 522 and the second signal 532 can reduce the accuracy of the regulated power applied to the plasma. In certain such embodiments, the DSP 545 reduces the noise by using real-time digital frequency filtering algorithms. Examples of filtering techniques in accordance with embodiments include, but are not limited to, finite impulse response (FIR)

and infinite impulse response (IIR). Such algorithms are described in "DSP Applications Using C and the TMS320C6X DSK," John Wiley & Sons, ISBN: 0471207543, and "DSP System Design Using the TMS320C6000, Prentice Hall, ISBN: 0130910317. In certain embodiments, the DSP 545 is programmable to provide filtering algorithms to remove unwanted high frequency components as well as unwanted frequency components below the fundamental frequency of the applied pulses. In certain embodiments, the roll offs of the filtering algorithms attenuate preferably at approximately 20 dB per decade and most preferably at greater than approximately 20 dB per decade, where the pass band is at approximately 0 dB. The filter coefficients (e.g., attenuation, gain) are determined once the operating frequency and sampling frequency are selected.

In certain embodiments, the DSP 545 is programmable to identify plasma instability and to make adjustments to stabilize the plasma. As an example, filamentation instability due to an abnormal pressure change can be identified if the plasma impedance (V/I) falls below a predetermined threshold. The filamentation instability can also be identified if the current increases above a predetermined threshold or if the voltage falls below a predetermined threshold.

Although described above in connection with particular embodiments, it should be understood the descriptions of the embodiments are illustrative of the invention and are not intended to be limiting. Various modifications and applications may occur to those skilled in the art without departing from the true spirit and scope of the invention as defined in the appended claims.

What is claimed is:

1. A sterilization system that applies power to a plasma within a chamber to remove gas or vapor species from an article, the sterilization system comprising a power feedback control system for controlling the power applied to the plasma, the power feedback control system comprising:
    a current monitor adapted to produce a first signal indicative of a current applied to the plasma within the chamber;
    a voltage monitor adapted to produce a second signal indicative of a voltage applied to the plasma within the chamber;
    a power control module comprising a programmable digital signal processor, the digital signal processor adapted to receive and process the first signal and the second signal by multiplying the current and the voltage and producing a third signal indicative of the product of the current and the voltage; and
    a plasma generator coupled to the power control module and adapted to adjust, in response to the third signal, the power applied to the plasma within the chamber.

2. The sterilization system as described in claim 1, wherein the plasma is a non-equilibrium plasma.

3. The sterilization system as described in claim 1, wherein the plasma generator comprises the current monitor and the voltage monitor.

4. The sterilization system as described in claim 1, wherein the digital signal processor is programmable to regulate the power to be within approximately 5% of a predetermined average power value.

5. The sterilization system as described in claim 1, wherein the digital signal processor is programmable to regulate the power to be within approximately 0.1% of a predetermined average power value.

6. The sterilization system as described in claim 1, wherein the digital signal processor is programmable to monitor plasma impedance.

7. The sterilization system as described in claim 6, wherein the digital signal processor is programmable to provide impedance monitoring on a time frame between approximately 10 nanoseconds to approximately 1000 nanoseconds.

8. The sterilization system as described in claim 6, wherein the plasma generator applies current and voltage pulses to the plasma and comprises a pulse width monitor adapted to adjust the widths of the applied current and voltage pulses in response to the third signal, and the digital signal processor is programmable to provide intra-pulse impedance monitoring.

9. The sterilization system as described in claim 1, wherein the digital signal processor is programmable to provide open-circuit protection.

10. The sterilization system as described in claim 1, wherein the digital signal processor is programmable to provide short-circuit protection.

11. The sterilization system as described in claim 1, wherein the digital signal processor is programmable to detect plasma ignition on a time frame between approximately 10 nanoseconds to approximately 100 milliseconds.

12. The sterilization system as described in claim 1, wherein the digital signal processor is programmable to monitor plasma peak-to-peak voltages from approximately 0.1 V to approximately 20 kV.

13. The sterilization system as described in claim 1, wherein the digital signal processor is programmable to monitor plasma peak-to-peak voltages on a time frame between approximately 10 nanoseconds to approximately 1000 nanoseconds.

14. The sterilization system as described in claim 1, wherein the digital signal processor is programmable to monitor plasma peak-to-peak currents from approximately 0.1 A to approximately 100 A.

15. The sterilization system as described in claim 1, wherein the digital signal processor is programmable to monitor plasma peak-to-peak currents on a time frame between approximately 10 nanoseconds to approximately 1000 nanoseconds.

16. The sterilization system as described in claim 1, wherein the digital signal processor is programmable to predict plasma instability.

17. The sterilization system as described in claim 1, further comprising a temperature monitor coupled to the chamber and to the power control module, the power control module adapted to produce the third signal in further response to a signal from the temperature monitor.

18. The sterilization system as described in claim 1, further comprising a pressure monitor coupled to the chamber and to the power control module, the power control module adapted to produce the third signal in further response to a signal from the pressure monitor.

19. The sterilization system as described in claim 1, further comprising a sterilant concentration monitor coupled to the chamber and to the power control module, the power control module adapted to produce the third signal in further response to a signal from the sterilant concentration monitor.

20. A method of applying power to a plasma within a chamber to remove gas or vapor species from an article, the method comprising:
    producing a first signal indicative of a current applied to the plasma within the chamber;
    producing a second signal indicative of a voltage applied to the plasma within the chamber;
    producing a third signal in response to the first signal and the second signal, wherein the third signal is produced using a programmable digital signal processor that multiplies the current and the voltage and the third signal is indicative of the product of the current and the voltage; and adjusting the power applied to the plasma in response to the third signal.

21. A sterilization system that applies power to a plasma within a chamber to remove gas or vapor species from an article, the sterilization system comprising a power feedback control system for controlling the power applied to the plasma, the power having a waveform frequency, the power feedback control system comprising:

a current monitor adapted to produce a first signal indicative of a current applied to the plasma within the chamber;

a voltage monitor adapted to produce a second signal indicative of a voltage applied to the plasma within the chamber;

a power control module adapted to produce a third signal in response to the first signal and the second signal, the power control module having a processing speed faster than the inverse of the waveform frequency; and a plasma generator coupled to the power control module and adapted to adjust, in response to the third signal, the power applied to the plasma within the chamber.

22. The sterilization system as described in claim 21, wherein the power control module comprises a programmable digital signal processor.

23. The sterilization system as described in claim 21, wherein the processing speed is faster than one-half of the inverse of the waveform frequency.

24. A sterilization system that applies a power wavetrain to a plasma within a chamber to remove gas or vapor species from an article, the power wavetrain comprising a plurality of power pulses having a characteristic pulse period, the sterilization system comprising a power feedback control system for controlling the power applied to the plasma, the power feedback control system comprising:

a current monitor adapted to produce a first signal indicative of a current applied to the plasma within the chamber;

a voltage monitor adapted to produce a second signal indicative of a voltage applied to the plasma within the chamber, the first and second signals produced on a time scale shorter than the characteristic pulse period;

a power control module adapted to monitor the first signal and the second signal and to produce a third signal in response to the first signal and the second signal, the third signal produced on a time scale shorter than the characteristic pulse period; and a plasma generator coupled to the power control module and adapted to adjust, in response to the third signal, the power applied to the plasma within the chamber, wherein the power applied to the plasma is adjusted on a time scale shorter than the characteristic pulse period, thereby providing intra-pulse monitoring and control of the power applied to the plasma.

25. The sterilization system as described in claim 24, wherein intra-pulse monitoring and control is provided during the entire power wavetrain.

* * * * *